United States Patent
Rebbaa et al.

(10) Patent No.: US 11,078,159 B2
(45) Date of Patent: Aug. 3, 2021

(54) COMPOUNDS AND METHODS FOR INHIBITING EMT PATHWAYS TO TREAT CANCER, ORGAN FIBROSIS AND METABOLIC DISORDERS

(71) Applicants: University of Pittsburgh—Of the Commonwealth System of Higher Education, Pittsburgh, PA (US); Universite Le Havre Normandie, Le Havre (FR)

(72) Inventors: Abdelhadi Rebbaa, Northvale, NJ (US); Sebastien Comesse, Yvetot (FR); Adam Daich, Cauville sur Mer (FR); Martin Lawson, Les Loges (FR); Catalin Pintiala, Lille (FR)

(73) Assignees: University of Pittsburgh—Of the Commonwealth System of Higher Education, Pittsburgh, PA (US); Universite Le Havre Normandie, Le Havre (FR)

( * ) Notice: Subject to any disclaimer, the term of this patent is extended or adjusted under 35 U.S.C. 154(b) by 0 days.

(21) Appl. No.: 16/487,770

(22) PCT Filed: Feb. 19, 2018

(86) PCT No.: PCT/US2018/018647
§ 371 (c)(1),
(2) Date: Aug. 21, 2019

(87) PCT Pub. No.: WO2018/156459
PCT Pub. Date: Aug. 30, 2018

(65) Prior Publication Data
US 2019/0375710 A1    Dec. 12, 2019

Related U.S. Application Data
(60) Provisional application No. 62/462,254, filed on Feb. 22, 2017.

(51) Int. Cl.
C07D 213/02    (2006.01)
A61P 35/00     (2006.01)

(52) U.S. Cl.
CPC ............ C07D 213/02 (2013.01); A61P 35/00 (2018.01)

(58) Field of Classification Search
CPC ............................... C07D 231/02; A16P 35/00
See application file for complete search history.

(56) References Cited

U.S. PATENT DOCUMENTS 9,649,300 B2    5/2017  Rebbaa et al.
2016/0200697 A1    7/2016  Rebbaa et al.

FOREIGN PATENT DOCUMENTS

EP    1 754 483    2/2007
WO    WO 2015/031109    3/2015

OTHER PUBLICATIONS

Mehrparvar, S., et al. "An efficient tandem approach for the synthesis of functionalized 2-pyridone-3-carboxylic acids using three-component reaction in aqueous media." Mol. Divers (2014), vol. 18, pp. 535-543. (Year: 2014).*
Coutinho et al Indian Journal of Chemistry, Section B: Organic Chemistry Including Medicinal Chemistry , 1992, (9), p. 573-577.*
Pintiala et al Tetrahedron Letters, 2013, 54, 2853-2857.*
Poudel et al Green Chem. 2015, 17, 4579-4586.*
Bautista et al RSC Advances 2016, 6, 82321-82329.*
Seixas et al ChemistrySelect2016, 1, 318-322.*
Eliel and Wilen, Stereochemistry of Organic Compounds, 1994, John Wiley and Sons, Inc. pp. 13, 481, 1208.*
International Search Report and Written Opinion issued for International Application No. PCT/US2018/018647 dated May 24, 2018.
Lepitre et al., "Competitive intramolecular C—C vs. C—O bond coupling reactions toward C6 ring-infused 2-pyridone synthesis," *Organic & Biomolecular Chemistry*, 14(14): 3564-3573, Mar. 7, 2016.
Lepitre et al., "Original Mitsunobu-triggered sequence involved in a one-pot domino process toward tetracyclic systems bearing a Bis-N, O-acetal junction," *The Journal of Organic Chemistry*, 81(19): 8837-8849, Sep. 16, 2016.
Mehrparvar et al., "An efficient tandem approach for the synthesis of functionalized 2-pyridone-3-carboxylic acids using three-component reaction in aqueous media," *Molecular Diversity*, 18(3): 535-543, Aug. 1, 2014.

(Continued)

*Primary Examiner* — John Mabry
(74) *Attorney, Agent, or Firm* — Kalrquist Sparkman, LLP

(57) ABSTRACT

A compound, or a pharmaceutically acceptable salt or isomer thereof, of Formula I:

Formula I

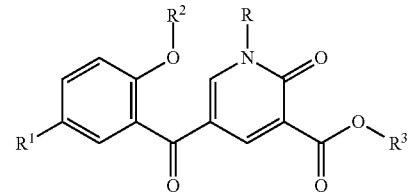

wherein R is hydrogen, alkyl, substituted alkyl, alkenyl, or substituted alkenyl;
$R^1$ is hydrogen, alkoxy, or substituted alkoxy;
$R^2$ is hydrogen, alkyl, or substituted alkyl; and
$R^3$ is hydrogen, alkyl, or substituted alkyl.

19 Claims, 5 Drawing Sheets

(56) References Cited

OTHER PUBLICATIONS

Pesquet et al., "Use of the cascade α-oxo-amidoalkylation/transposition/π-cationic cyclization of N-acyliminium ions in the synthesis of novel fused heterocyclic N,O-actals,"*ARKIVOC*, pp. 27-40, Mar. 10, 2010.

Pintiala et al., "A versatile domino process for the synthesis of substituted 3-aminomethylene-chromanones and 2-pyridones catalyzed by CsF," *Tetrahedron Letters*, vol. 54, pp. 2853-2857, Apr. 2, 2013.

Cameron et al., "Recent progress in the identification of adenosine monophosphate activated protein kinase (AMPK) activators," *Bioorganic & Medicinal Chemistry Letters*, 26(21): 5139-5148, Nov. 1, 2016.

Pesquet et al., "An unusual polyheterocyclic diversity by the π-cyclisation of N-carbamoyl-iminium ion, with or without tandem N,N-acetal cleavage, from spiro(imi-dazolidinoquinazolinones)," *Synthesis*, No. 9, pp. 1389-1396, Apr. 16, 2008.

Rajkumar et al., "Facile construction of novel heterocyclic compounds: three-component, one-pot synthesis of 2-hydroxybenzoyl-1,2-dihydropyridine-3-carboxylates, ketones, pyridone-3-carboxylates and benzopyrido-1,3-oxazole-4-carboxylates," *RSC Adv.*, 5(90): 73850-73858, Aug. 24, 2015.

Sriwijitkamol et al., "Advances in the development of AMPK-activating compounds," *Expert Opinion on Drug Discovery*, 3(10): 1167-1176, Sep. 28, 2008.

Bari et al., "A Facile One-Pot Synthesis and Anticancer Evaluation of Novel Substituted 1,2-Dihydropyridine and 1,2,3,4-Tetrahydropyrimidine Analogues," *Journal of Heterocyclic Chemistry*, vol. 53, pp. 377-382, Mar. 31, 2015.

Extended European Search Report issued for EPC Application No. 18757741.6 dated Dec. 4, 2020.

\* cited by examiner

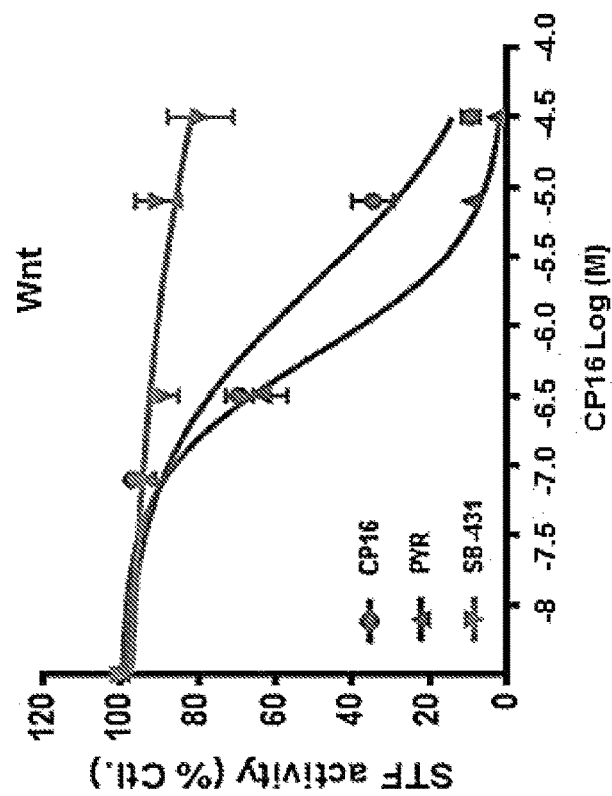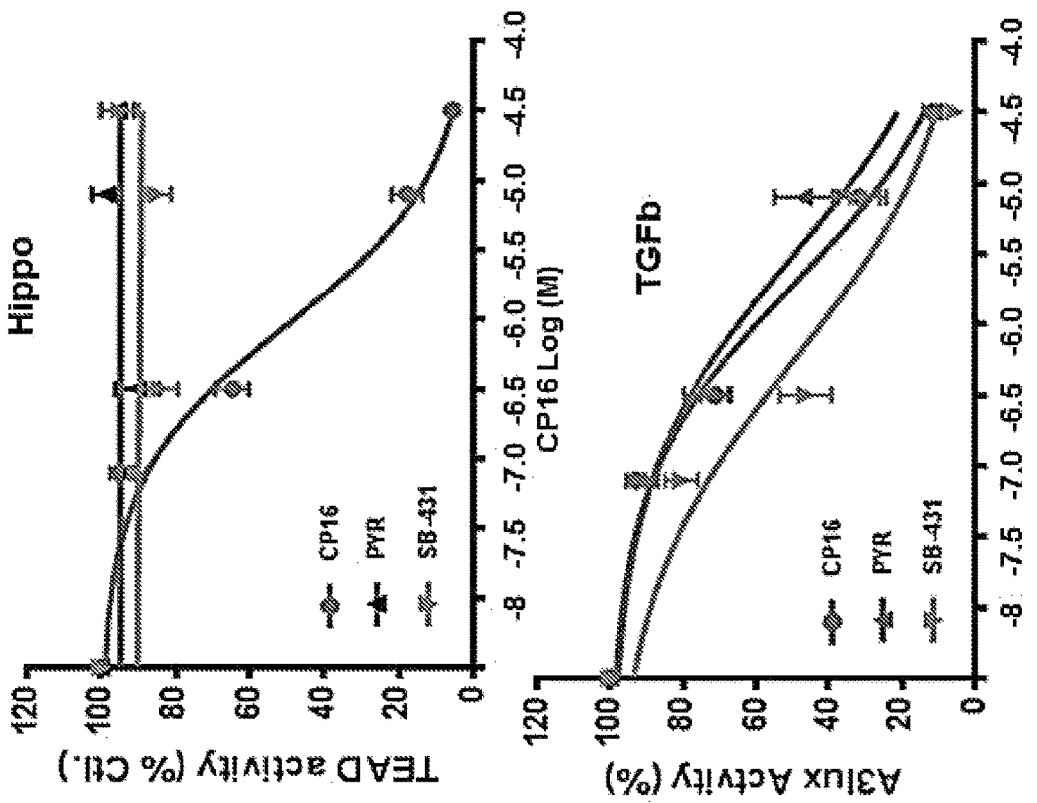

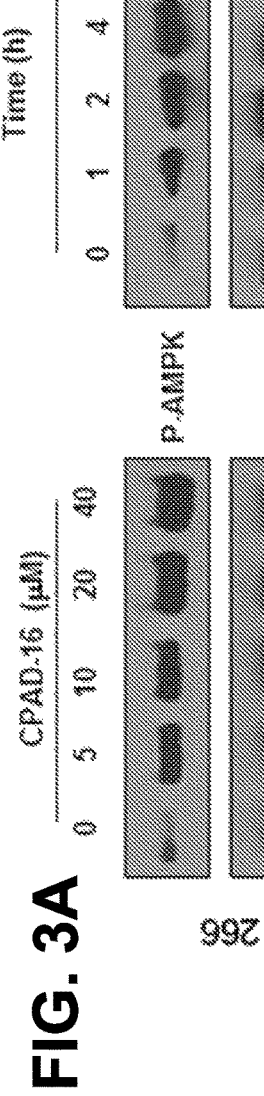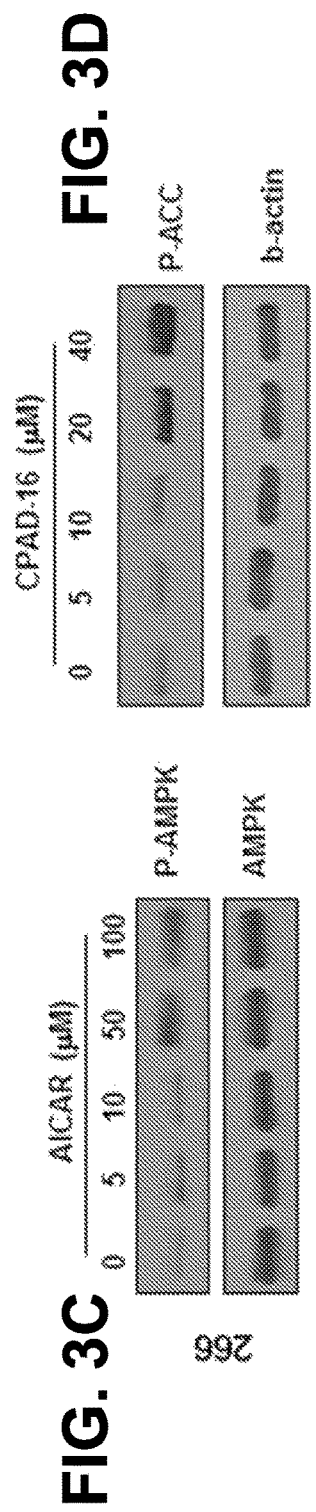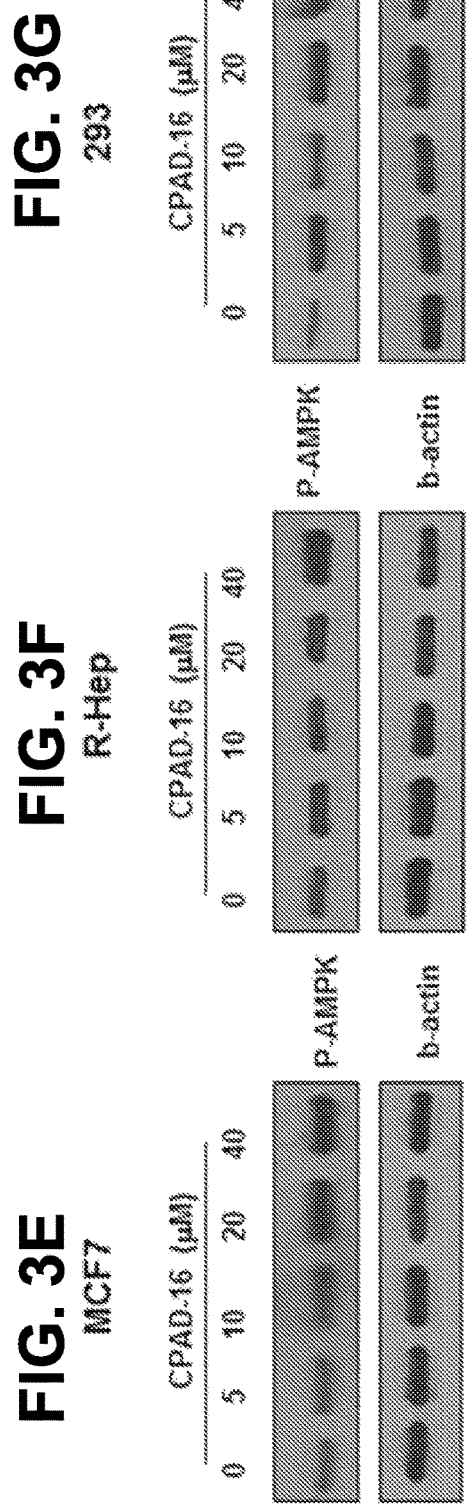

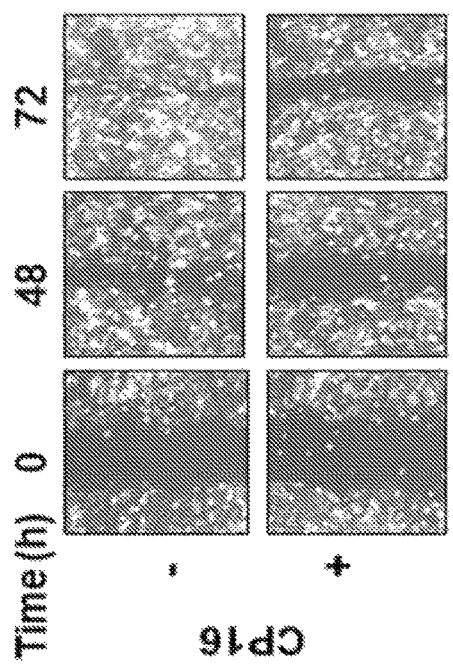
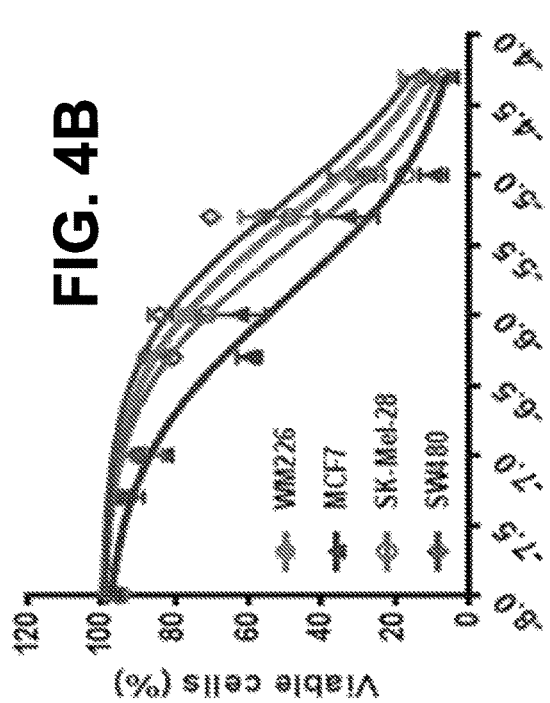
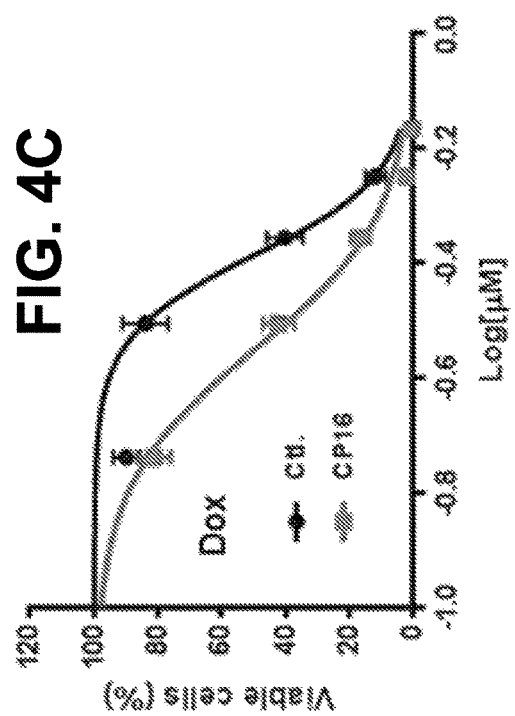
FIG. 4A
FIG. 4B
FIG. 4C

COMPOUNDS AND METHODS FOR INHIBITING EMT PATHWAYS TO TREAT CANCER, ORGAN FIBROSIS AND METABOLIC DISORDERS

CROSS REFERENCE TO RELATED APPLICATIONS

This is the U.S. National Stage of International Application No. PCT/US2018/018647, filed Feb. 19, 2018, which was published in English under PCT Article 21(2), which application in turn claims the benefit of U.S. Provisional Application No. 62/462,254, filed Feb. 22, 2017, which is herein incorporated by reference in its entirety.

BACKGROUND

Epithelial-mesenchymal transition (EMT) is a transdifferentiation process by which epithelial cells undergo changes in morphology and cell-cell junction, to detach from each other and acquire invasive abilities. EMT is recognized to play key roles in processes such as wound healing, tissue fibrosis and cancer. With regard to cancer, EMT not only allows cancer cells to disseminate from the primary tumor but also confers protection from cell death, facilitates immune escape and induces resistance to therapy. TGF beta and Wnt signaling are considered the major drivers of EMT, however recent findings indicated that both of these pathways are regulated by a third one named Hippo. In fact, downstream mediators of this pathway namely YAP, TAZ and TEAD were found to act independently or as co-activators for both beta catenin/TCF and Smad complexes to induce EMT. Based on this, the development of approaches to inhibit activity of the Hippo pathway is expected to have applications for the treatment of EMT-associated diseases.

The adenosine monophosphate-activated protein kinase (AMPK) is an important regulatory protein for cellular energy balance and is considered a master switch of glucose and lipid metabolism in various organs, especially in skeletal muscle and liver. Recent evidence indicated that the function of this enzyme extends beyond the canonical metabolic pathway to include tumor suppression, cell polarity, fibrosis, and even aging. Concerning its role in metabolism, AMPK was originally defined as the upstream kinase for the critical metabolic enzymes Acetyl-CoA carboxylase (ACC1 & ACC2) and HMG-CoA reductase, which serve as the rate limiting steps for fatty-acid and sterol synthesis in a wide-variety of eukaryotes. In specialized tissues such as muscle and fat, AMPK regulates glucose uptake via the RabGAP TBC1D1, which along with its homolog TBC1D4 (AS160), play key roles in GLUT4 trafficking following exercise and insulin. In skeletal muscles, AMPK stimulates glucose transport and fatty acid oxidation, and in the liver, it augments fatty acid oxidation and decreases glucose output, cholesterol and triglyceride synthesis. These metabolic effects induced by AMPK are associated with lowering blood glucose levels in hyperglycemic individuals.

In conditions where nutrients are scarce, AMPK acts as a metabolic checkpoint inhibiting cellular growth. The most thoroughly described mechanism by which AMPK regulates cell growth is via suppression of the mammalian target of rapamycin complex 1 (mTORC1) pathway. This occurs by direct phosphorylation of the tumor suppressor TSC2 and also through direct phosphorylation of Raptor (regulatory associated protein of mTOR), on two conserved serines, which blocks the ability of the mTORC1 kinase complex to phosphorylate its substrates. mTORC1 has been shown to induce cell growth through inhibition of autophagy, a cellular process of "self engulfment" in which the cell breaks down its own organelles (macroautophagy) and cytosolic components (microautophagy) to ensure sufficient metabolites when nutrients run low. In addition to inhibitory phosphorylation of mTORC1, studies from a number of laboratories in the past few years have revealed that AMPK directly activates the ULK1, a kinase with a critical role in autophagy and mitochondrial homeostasis.

AMPK has also been shown to mediate the tumor suppressive function of the liver kinase LKB1, a gene associated with Peutz-Jeghers syndrome, an autosomal dominant genetic disorder characterized by multiple hamartomatous polyps (benign overgrowth of differentiated tissues) in the gastrointestinal tract and a markedly increased risk of gastrointestinal adenocarcinomas, of lung adenocarcinomas, 19% of squamous cell carcinomas and 20% of cervical carcinomas and other cancers In addition to the well-established role for AMPK in cell growth and metabolism, recent studies suggested that AMPK may control cell polarity and cytoskeletal dynamics. In fact, it has been known for some time that the AMPK upstream effector, LKB1 plays a critical role in cell polarity from simpler to complex eukaryotes. These studies also supported a role for AMPK in cell polarity as a loss of this enzyme in *Drosophila* results in altered polarity and its activation in mammalian MDCK cells was needed for proper re-polarization and tight junction formation.

Loss of cell polarity is a consequence of epithelial mesenchymal transition (EMT). During this process epithelial cells lose their intercellular connections (tight junctions and adherens junction), change morphology and separate from each other. The affected cells generally adopt a spindly (elongated) morphology that facilitates their migration to distant sites. EMT has been shown to play key roles in development, cancer and organ fibrosis. AMPK has been shown to exert its inhibitory effect on renal fibrosis induced by TGF-$\beta$, angiotensin II, aldosterone, and high glucose, principally through inhibition of EMT. Moreover, the AMPK activator Metformin also suppresses EMT and thiazolidinediones were found to improve hepatic fibrosis by activating the AMPK signaling pathway in rats with non-alcoholic steatohepatitis. AMPK also plays a role in cardiac remodeling, as it pertains to diabetic cardiomyopathy, cardiac hypertrophy, and heart failure, suggesting that there might be therapeutic value in targeting the AMPK signaling pathway to treat cardiovascular diseases. In fact, dysfunction of the AMPK signaling pathway has been shown to be involved in the genesis and development of various cardiovascular diseases, including atherosclerosis, hypertension and stroke. AMP-activated protein kinase activator AICAR acutely lowers blood pressure and relaxes isolated resistance arteries of hypertensive rats. Adiponectin, a hormone AMPK activator has been shown to inhibit doxorubicin-induced cardiotoxicity.

In addition to its well established role in metabolism, cancer and fibrosis, AMPK has also been shown to affect other aging-associated diseases such as inflammation, neurodegeneration, sarcopenia and even the aging process itself. This is exemplified by the findings that the AMPK activator AICAR inhibits TNF-a- and IL-1a-induced NF—B reporter gene expression dose dependently in immune cells and inducible nitric oxide synthase and cyclooxygenase-2 (COX-2) expression in stimulated macrophages. Activators of AMPK were also reported to inhibit chemotaxis in the monocyte-like cell line U937. In addition, AICAR profoundly inhibited lipopolysaccharide and IFN-$\alpha$-stimulated production of the proinflammatory molecules nitric oxide synthase, COX-2, and IL-6. With regard to neurodegeneration, emerging studies indicate that AMPK signaling can regulate tau protein phosphorylation and amyloidogenesis, the major hallmarks of AD. AMPK is also a potent activator of autophagic degradation which seems to be suppressed in AD.

Sarcopenia is characterized by a muscle atrophy (a decrease in the size of the muscle), along with a reduction in muscle tissue "quality," caused by such factors as replacement of muscle fibers with fat, an increase in fibrosis, changes in muscle metabolism, oxidative stress, and degeneration of the neuromuscular junction. Combined, these changes lead to progressive loss of muscle function and frailty. Agents that activate AMPK such as AICAR and GW501516 induced improvements in disease phenotype, including an increase in overall behavioral activity and significant gains in forelimb and hind limb strength.

Many studies with lower organisms have revealed that increased AMPK activity can extend the lifespan. Experiments in mammals have demonstrated that AMPK controls autophagy through mTOR and ULK1 signaling which augment the quality of cellular housekeeping. Moreover, AMPK-induced stimulation of FoxO/DAF-16, Nrf2/SKN-1, and SIRT1 signaling pathways and improves cellular stress resistance. Emerging studies indicate that the responsiveness of AMPK signaling clearly declines with aging. The loss of sensitivity of AMPK activation to cellular stress impairs metabolic regulation, increases oxidative stress and reduces autophagic clearance. These age-related changes activate immune cells, triggering a low-grade inflammation and metabolic disorders, leading to acceleration of aging. In contrast, evidence was provided that chronic feeding of rodents with AMPK agonists improves muscle endurance, reduces metabolic diseases, allows proper circadian regulation, and suppresses tumorigenesis. These findings strengthen AMPK's position as a main beacon of hope for the prevention and/or treatment of the current epidemic of metabolic and age-related diseases.

AMPK is generally activated in response to nutrient deprivation, exercise and also by hormones such as leptin, grelin, and adiponectin. Two classes of oral antihyperglycemic drugs (biguanidines and thiazolidinediones) have been shown to exert some of their therapeutic effects by directly or indirectly activating AMPK. Novel pharmacological agents such as the prototypical activator 5-aminoimidazole-4-carboxamide 1-D-ribonucleoside (AICAR) and Abbott A769662 have recently been introduced. Interestingly, oral administration of AICAR to eight-week-old male C57B/6J mice was reported to mediate a 44% increase in endurance without exercise in untrained mice, leading to speculation that these type of compounds may be considered as exercise mimetics. However, side effects and an acquired resistance to these drugs emphasize the need for the development of novel and efficacious AMPK activators.

SUMMARY

Disclosed herein are compounds, or pharmaceutically acceptable salts or isomers thereof, of Formula I:

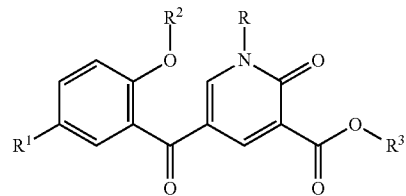

wherein R is hydrogen, alkyl, substituted alkyl, alkenyl, or substituted alkenyl;
$R^1$ is hydrogen, alkoxy, or substituted alkoxy;
$R^2$ is hydrogen, alkyl, or substituted alkyl; and
$R^3$ is hydrogen, alkyl, or substituted alkyl.

Also disclosed herein is a method for treating an epithelial-mesenchymal transition-associated disorder or an adenosine monophosphate-activated protein kinase-associated disorder in a subject, comprising administering to the subject in need thereof a therapeutically effective amount of a compound disclosed herein.

Further disclosed herein is a method of inhibiting at least one of a Hippo, Wnt, and TGF beta pathway in a subject, comprising administering to the subject a compound as disclosed herein.

Additionally disclosed herein is a method of inhibiting an epithelial-mesenchymal transition in a cell, comprising contacting the cell with a compound disclosed herein.

Also disclosed herein is a method of activating an adenosine monophosphate-activated protein kinase in a cell, comprising contacting the cell with a compound disclosed herein.

The foregoing will become more apparent from the following detailed description, which proceeds with reference to the accompanying figures.

BRIEF DESCRIPTION OF THE DRAWINGS

FIGS. 1A-1C. CPADAML16 is a common inhibitor of Wnt (FIG. 1C), TGF beta (FIG. 1B), and Hippo (FIG. 1A). 293 cells were transfected with luciferase reporters corresponding to each pathway and then exposed to CPAD-AML16, the Wnt inhibitor Pyrvinium (PYR) or the TGF beta inhibitor SB-431 at the indicated concentrations. After 24 hours, the cells were lysed and luciferase activity measured. Data represents average of three replicates ±SE.

FIG. 2A. Effect of CPADAML16 on Hippo pathway transduces YAP, TAZ and TEAD measured by Western blot. FIG. 2B. Possible signaling pathways leading to degradation of TAZ. The effects of CPADAML16 on the Mst/Lats kinases and the Akt/GSK3 beta axis are shown in FIGS. 2C and 2D, respectively.

FIGS. 3A-3G. Effect of CPADAML16 on MAP kinase. FIGS. 3A and 3B. Dose and time dependent effects of CPADAML16 on phosphorylation of AMPK. FIG. 3C. Effect of AICAR on phosphorylation of AMPK. FIG. 3D. Effect of CPADAML16 on phosphorylation of AMPK downstream target ACC. FIGS. 3E-3G. Confirmation CPADAML16-induced AMPK phosphorylation in different cell lines.

FIGS. 4A-4C. Inhibition of cell migration, proliferation and resistance to therapy by CPADAML16.

FIG. 4A. Cell monolayer scratch depicting inhibition of cell migration by CPADAML16. FIG. 4B. Effect on cell proliferation measured after 5 days of incubation. FIG. 4C. Cell response to doxorubicin was measured in the presence and absence of CPADAML16. Data in FIG. 4C represent average of three determinations ±SE.

DETAILED DESCRIPTION

Terminology

Figure 2B:
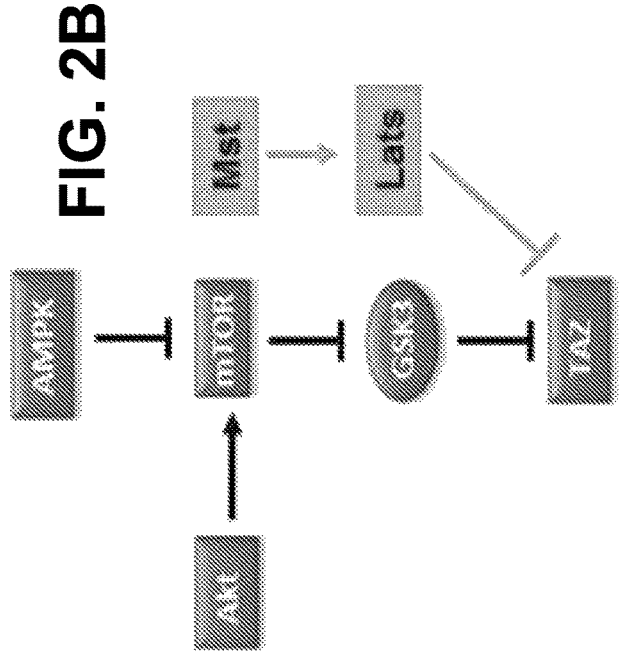
FIGS. 2A-2D. Putative mechanism.

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

Administration" as used herein is inclusive of administration by another person to the subject or self-administration by the subject.

"Alkenyl" refers to a cyclic, branched or straight chain group containing only carbon and hydrogen, and contains one or more double bonds that may or may not be conjugated. Alkenyl groups may be unsubstituted or substituted. "Lower alkenyl" groups contain one to six carbon atoms.

The term "alkoxy" refers to a straight, branched or cyclic hydrocarbon configuration and combinations thereof, including from 1 to 20 carbon atoms, preferably from 1 to 8 carbon atoms (referred to as a "lower alkoxy"), more preferably from 1 to 4 carbon atoms, that include an oxygen atom at the point of attachment. An example of an "alkoxy group" is represented by the formula —OR, where R can be an alkyl group, optionally substituted with an alkenyl, alkynyl, aryl, aralkyl, cycloalkyl, halogenated alkyl, alkoxy or heterocycloalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, alkenyl, or carboxyl. For example, a lower alkyl or ($C_1$-$C_6$)alkyl can be methyl, ethyl, propyl, isopropyl, butyl, iso-butyl, sec-butyl, pentyl, 3-pentyl, or hexyl; ($C_3$-$C_6$)cycloalkyl can be cyclopropyl, cyclobutyl, cyclopentyl, or cyclohexyl; ($C_3$-$C_6$)cycloalkyl($C_1$-$C_6$)alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; ($C_1$-$C_6$)alkoxy can be methoxy, ethoxy, propoxy, isopropoxy, butoxy, isobutoxy, sec-butoxy, pentoxy, 3-pentoxy, or hexyloxy; ($C_2$-$C_6$)alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; ($C_2$-$C_6$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; ($C_1$-$C_6$) alkanoyl can be acetyl, propanoyl or butanoyl; halo($C_1$-$C_6$) alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy($C_1$-$C_6$)alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_1$-$C_6$)alkylthio can be methylthio, ethylthio, propylthio, isopropylthio, butylthio, isobutylthio, pentylthio, or hexylthio; ($C_2$-$C_6$) alkanoyloxy can be acetoxy, propanoyloxy, butanoyloxy, isobutanoyloxy, pentanoyloxy, or hexanoyloxy.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

The term "aralkyl" refers to an alkyl group wherein an aryl group is substituted for a hydrogen of the alkyl group. An example of an aralkyl group is a benzyl group.

"Aryl" refers to a monovalent unsaturated aromatic carbocyclic group having a single ring (e.g., phenyl) or multiple condensed rings (e.g., naphthyl or anthryl), which can optionally be unsubstituted or substituted. A "heteroaryl group," is defined as an aromatic group that has at least one heteroatom incorporated within the ring of the aromatic group. Examples of heteroatoms include, but are not limited to, nitrogen, oxygen, sulfur, and phosphorous. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. The aryl or heteroaryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl or heteroaryl group can be unsubstituted.

"Aryloxy" or "heteroaryloxy" refers to a group of the formula —OAr, wherein Ar is an aryl group or a heteroaryl group, respectively.

The term "co-administration" or "co-administering" refers to administration of a compound disclosed herein with at least one other therapeutic or diagnostic agent within the same general time period, and does not require administration at the same exact moment in time (although co-administration is inclusive of administering at the same exact moment in time). Thus, co-administration may be on the same day or on different days, or in the same week or in different weeks.

The terms "halogenated alkyl" or "haloalkyl group" refer to an alkyl group with one or more hydrogen atoms present on these groups substituted with a halogen (F, Cl, Br, I).

"Inhibiting" refers to inhibiting the full development of a disease or condition. "Inhibiting" also refers to any quantitative or qualitative reduction in biological activity or binding, relative to a control.

"N-heterocyclic" refers to mono or bicyclic rings or ring systems that include at least one nitrogen heteroatom. The rings or ring systems generally include 1 to 9 carbon atoms in addition to the heteroatom(s) and may be saturated, unsaturated or aromatic (including pseudoaromatic). The term "pseudoaromatic" refers to a ring system which is not strictly aromatic, but which is stabilized by means of delocalization of electrons and behaves in a similar manner to aromatic rings. Aromatic includes pseudoaromatic ring systems, such as pyrrolyl rings.

Examples of 5-membered monocyclic N-heterocycles include pyrrolyl, H-pyrrolyl, pyrrolinyl, pyrrolidinyl, oxazolyl, oxadiazolyl, (including 1,2,3 and 1,2,4 oxadiazolyls) isoxazolyl, furazanyl, thiazolyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls), and dithiazolyl. Examples of 6-membered monocyclic N-heterocycles include pyridyl, pyrimidinyl, pyridazinyl, pyrazinyl, piperidinyl, morpholinyl, thiomorpholinyl, piperazinyl, and triazinyl. The heterocycles may be optionally substituted with a broad range of substituents, and preferably with $C_{1-6}$ alkyl, $C_{1-6}$ alkoxy, $C_{2-6}$ alkenyl, $C_{2-6}$ alkynyl, halo, hydroxy, mercapto, trifluoromethyl, amino, cyano or mono or di($C_{1-6}$alkyl)amino. The N-heterocyclic group may be fused to a carbocyclic ring such as phenyl, naphthyl, indenyl, azulenyl, fluorenyl, and anthracenyl.

Examples of 8, 9 and 10-membered bicyclic heterocycles include 1H thieno[2,3-c]pyrazolyl, indolyl, isoindolyl, benzoxazolyl, benzothiazolyl, benzisoxazolyl, benzisothiazolyl, benzimidazolyl, indazolyl, isoquinolinyl, quinolinyl, quinoxalinyl, purinyl, cinnolinyl, phthalazinyl, quinazolinyl, quinoxalinyl, benzotriazinyl, and the like. These heterocycles may be optionally substituted, for example with $C_{1-6}$ alkyl, $C_{1-6}$ alkoxy, $C_{2-6}$ alkenyl, $C_{2-6}$ alkynyl, halo, hydroxy, mercapto, trifluoromethyl, amino, cyano or mono or di($C_{1-6}$alkyl)amino. Unless otherwise defined optionally substituted N-heterocyclics includes pyridinium salts and the N-oxide form of suitable ring nitrogens.

The term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

"Substituted" or "substitution" refers to replacement of a hydrogen atom of a molecule or an R-group with one or more additional R-groups. Unless otherwise defined, the term "optionally-substituted" or "optional substituent" as used herein refers to a group which may or may not be further substituted with 1, 2, 3, 4 or more groups, preferably 1, 2 or 3, more preferably 1 or 2 groups. The substituents may be selected, for example, from $C_{1-6}$ alkyl, $C_{2-6}$ alkenyl, $C_{2-6}$ alkynyl, $C_{3-8}$ cycloalkyl, hydroxyl, oxo, $C_{1-6}$ alkoxy, aryloxy, $C_{1-6}$alkoxyaryl, halo, $C_{1-6}$alkylhalo (such as $CF_3$ and $CHF_2$), $C_{1-6}$alkoxyhalo (such as $OCF_3$ and $OCHF_2$), carboxyl, esters, cyano, nitro, amino, substituted amino, disubstituted amino, acyl, ketones, amides, aminoacyl, substituted amides, disubstituted amides, thiol, alkylthio, thioxo, sulfates, sulfonates, sulfinyl, substituted sulfinyl, sulfonyl, substituted sulfonyl, sulfonylamides, substituted sulfonamides, disubstituted sulfonamides, aryl, ar$C_{1-6}$alkyl, heterocyclyl and heteroaryl wherein each alkyl, alkenyl, alkynyl, cycloalkyl, aryl and heterocyclyl and groups containing them may be further optionally substituted. Optional substituents in the case N-heterocycles may also include but are not limited to $C_{1-6}$alkyl i.e. N—$C_{1-3}$alkyl, more preferably methyl particularly N-methyl.

A "therapeutically effective amount" refers to a quantity of a specified agent sufficient to achieve a desired effect in a subject being treated with that agent. Ideally, a therapeutically effective amount of an agent is an amount sufficient to inhibit or treat the disease or condition without causing a substantial cytotoxic effect in the subject. The therapeutically effective amount of an agent will be dependent on the subject being treated, the severity of the affliction, and the manner of administration of the therapeutic composition.

"Treatment" refers to a therapeutic intervention that ameliorates a sign or symptom of a disease or pathological condition after it has begun to develop, or administering a compound or composition to a subject who does not exhibit signs of a disease or exhibits only early signs for the purpose of decreasing the risk of developing a pathology or condition, or diminishing the severity of a pathology or condition. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" refers to inhibiting the full development of a disease, for example, in a subject who is at risk for a disease. "Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition.

"Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's Pharmaceutical Sciences, Mack Publishing Co., Easton, Pa. (19th Edition).

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

"Pharmaceutically acceptable esters" includes those derived from compounds described herein that are modified to include a carboxyl group. An in vivo hydrolysable ester is an ester, which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, C.sub.1-4 alkyl, or C.sub.1-4 alkoxy) or amino); sulphonate esters, such as alkyl- or aralkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocyclyl above. Pharmaceutically acceptable esters thus include $C_1$-$C_{22}$ fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and especially valyl.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of a compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. F or a general discussion of prodrugs involving esters see Svensson and Tunek, *Drug Metabolism Reviews* 165 (1988) and Bundgaard, *Design of Prodrugs*, Elsevier (1985).

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Protected derivatives of the disclosed compounds also are contemplated. A variety of suitable protecting groups for use with the disclosed compounds are disclosed in Greene and Wuts, Protective Groups in Organic Synthesis; 3rd Ed.; John Wiley & Sons, New York, 1999.

In general, protecting groups are removed under conditions that will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts, Protective Groups in Organic Synthesis; 3rd Ed.; John Wiley & Sons, New York, 1999. When an amine is deprotected, the resulting salt can readily be neutralized to yield the free amine. Similarly, when an acid moiety, such as a phosphonic acid moiety is unveiled, the compound may be isolated as the acid compound or as a salt thereof.

Particular examples of the presently disclosed compounds may include one or more asymmetric centers; thus these compounds can exist in different stereoisomeric forms. Accordingly, compounds and compositions may be provided as individual pure enantiomers or as stereoisomeric mixtures, including racemic mixtures. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form. The presently disclosed compounds can have at least one asymmetric center or geometric center, cis-trans center (C═C, C═N). All chiral, diasteromeric, racemic, meso, rotational and geometric isomers of the structures are intended unless otherwise specified. The compounds can be isolated as a single isomer or as mixture of isomers. All tautomers of the compounds are also considered part of the disclosure. The presently disclosed compounds also includes all isotopes of atoms present in the compounds, which can include, but are not limited to, deuterium, tritium, $^{18}F$, etc Overview The present disclosure concerns the discovery of small molecules inhibitors of major EMT pathways particularly those mediated by TGF beta, Wnt and Hippo. These pathways are known to play key roles in the induction of epithelial-mesenchymal transition (EMT) a cellular process responsible for cancer metastasis, resistance to therapy and organ fibrosis. Recently, both Wnt and TGF beta signalling were found to be regulated by the Hippo pathway, suggesting that targeting the latter may have a better therapeutic outcome in treating EMT-associated disorders. In a search for putative inhibitors of the Hippo pathway, a luciferase reporter system was used to screen a series of chemical compounds. This led to the identification of a candidate molecule (CPADAML16) with a remarkable inhibitory activity against Hippo as well as Wnt and TGF beta pathways. CPADAML16 suppressed cancer cell ability to undergo EMT, to proliferate and to become drug resistant. Investigation of the underlying mechanism led to the finding that CPADAML16 induces degradation of the Hippo transducer TAZ mainly by activating AMPK upstream of the GSK3 beta associated degradation complex. CPADAML16 exerted a strong anti-tumor activity in a xenograft mice model with no noticeable toxicity. Since EMT is also known to play a key role in organ fibrosis, our findings suggest that in addition to its anti-cancer function, CPADAML16 may have potential applications for the treatment/prevention of fibrotic and metabolic diseases.

In certain embodiments, the compounds disclosed herein are activators of the tumor suppressor kinase AMPK suggesting that these type of compounds may have applications for treating not only EMT associated pathologies such as cancer and fibrosis, but also other diseases associated with AMPK. The compounds may act as activators of tumor suppressor kinases (AMPK and Mst/Lats), leading to activation of the GSK3 beta associated degradation complex, which is responsible for degradation of TAZ and other EMT inducing transcription factors.

Compounds Disclosed herein are compounds, or pharmaceutically acceptable salts or isomers thereof, of Formula I:

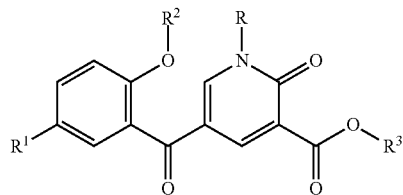

wherein R is hydrogen, alkyl, substituted alkyl, alkenyl, or substituted alkenyl;
$R^1$ is hydrogen, alkoxy, or substituted alkoxy;
$R^2$ is hydrogen, alkyl, or substituted alkyl; and
$R^3$ is hydrogen, alkyl, or substituted alkyl.

In certain embodiments, R is a $C_1$-$C_6$ alkyl; or a substituted alkyl of the structure —$(CH_2)_a$—Ar, wherein a is 1 to 6 and Ar is an aryl, substituted aryl, heteroaryl or substituted heteroaryl. In certain embodiments, Ar is phenyl or substituted phenyl (e.g., phenyl substituted with at least one halogen, alkoxy, and/or alkyl). In certain embodiments, Ar is an O-heteroaryl, an S-heteroaryl, or a N-heteroaryl. In certain embodiments, R is benzyl or substituted benzyl (e.g., halo-substituted benzyl, alkoxy-substituted benzyl, or alkyl-substituted benzyl). In certain embodiments, R is benzyl. In certain embodiments, R is not hydrogen.

In certain embodiments, $R^1$ is hydrogen. In certain embodiments, $R^1$ is —O—Ar, wherein Ar is an aryl, substituted aryl, heteroaryl or substituted heteroaryl. In certain embodiments, Ar is phenyl or substituted phenyl (e.g., phenyl substituted with at least one halogen, alkoxy, and/or alkyl).

In certain embodiments, $R^2$ is hydrogen. In certain embodiments, $R^2$ is $C_1$-$C_6$ alkyl.

In certain embodiments, $R^3$ is $C_1$-$C_6$ alkyl. In certain embodiments, $R^3$ is ethyl.

In certain embodiments, at least one of R, $R^1$, $R^2$ or $R^3$ is not hydrogen.

Contemplated herein are any combinations of the R—$R^3$ groups disclosed above.

Pharmaceutical Compositions and Methods of Use

In certain embodiments, the compounds disclosed herein may be used for treating epithelial-mesenchymal transition (EMT)-associated disorders. Illustrative EMT features associated with cancer include metastasis enhanced proliferation and resistance to treatment. Illustrative cancers include skin cancer, breast cancer, colon cancer, lung cancer, or blood cancer. Illustrative EMT-associated fibrotic disorders include those that affect the liver, lung, kidney, heart, and the skin, amyotrophic lateral sclerosis, multiple sclerosis, tuberous sclerosis, thrombosis, neurofibromatosis, neuro-inflammation, inflammatory pain, and neuropathic pain.

In certain embodiments, the compounds disclosed herein may be co-administered with other anti-cancer agents for treating primary, metastatic and/or drug-resistant cancers.

The compounds disclosed herein may have applications in treating and/or preventing various disorders associated with AMPK including cancer, type 1 diabetes, type 2 diabetes, metabolic syndrome, atherosclerosis, dyslipidemia, mitochondrial disorders, sarcopenia, obesity, hypertension, cerebral ischemia, cognitive defect Alzheimer's disease, Parkinson's disease, Huntington's disease, schizophrenia, Friedrich's Ataxia, metabolic syndrome, atherosclerosis, dyslipidaemia, mitochondrial disorders, sarcopenia, obesity, hypertension, cerebral ischemia, organ fibrosis, amyotrophic lateral sclerosis, multiple sclerosis, tuberous sclerosis, neurofibromatosis, neuro-inflammation, inflammatory pain, neuropathic pain, epilepsy, virus infection (HIV, cytomegalovirus and hepatitis C), and aging associated disorders.

Another aspect of the disclosure includes pharmaceutical compositions prepared for administration to a subject and which include a therapeutically effective amount of one or more of the compounds disclosed herein. The therapeutically effective amount of a disclosed compound will depend on the route of administration, the species of subject and the physical characteristics of the subject being treated. Specific factors that can be taken into account include disease severity and stage, weight, diet and concurrent medications. The relationship of these factors to determining a therapeutically effective amount of the disclosed compounds is understood by those of skill in the art.

Pharmaceutical compositions for administration to a subject can include at least one further pharmaceutically acceptable additive such as carriers, thickeners, diluents, buffers, preservatives, surface-active agents and the like in addition to the molecule of choice. Pharmaceutical compositions can also include one or more additional active ingredients such as antimicrobial agents, anti-inflammatory agents, anesthetics, and the like. The pharmaceutically acceptable carriers useful for these formulations are conventional. *Remington's Pharmaceutical Sciences*, by E. W. Martin, Mack Publishing Co., Easton, Pa., 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical compositions disclosed herein include those formed from pharmaceutically acceptable salts and/or solvates of the disclosed compounds. Pharmaceutically acceptable salts include those derived from pharmaceutically acceptable inorganic or organic bases and acids. Particular disclosed compounds possess at least one basic group that can form acid-base salts with acids. Examples of basic groups include, but are not limited to, amino and imino groups. Examples of inorganic acids that can form salts with such basic groups include, but are not limited to, mineral acids such as hydrochloric acid, hydrobromic acid, sulfuric acid or phosphoric acid. Basic groups also can form salts with organic carboxylic acids, sulfonic acids, sulfo acids or phospho acids or N-substituted sulfamic acid, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and, in addition, with amino acids, for example with α-amino acids, and also with methanesulfonic acid, ethanesulfonic acid, 2-hydroxymethanesulfonic acid, ethane-1,2-disulfonic acid, benzenedisulfonic acid, 4-methylbenzenesulfonic acid, naphthalene-2-sulfonic acid, 2- or 3-phosphoglycerate, glucose-6-phosphate or N-cyclohexylsulfamic acid (with formation of the cyclamates) or with other acidic organic compounds, such as ascorbic acid.

Certain compounds include at least one acidic group that can form an acid-base salt with an inorganic or organic base. Examples of salts formed from inorganic bases include salts of the presently disclosed compounds with alkali metals such as potassium and sodium, alkaline earth metals, including calcium and magnesium and the like. Similarly, salts of acidic compounds with an organic base, such as an amine (as used herein terms that refer to amines should be understood to include their conjugate acids unless the context clearly indicates that the free amine is intended) are contemplated, including salts formed with basic amino acids, aliphatic amines, heterocyclic amines, aromatic amines, pyridines, guanidines and amidines. Of the aliphatic amines, the acyclic aliphatic amines, and cyclic and acyclic di- and tri-alkyl amines are particularly suitable for use in the disclosed compounds. In addition, quaternary ammonium counterions also can be used.

Particular examples of suitable amine bases (and their corresponding ammonium ions) for use in the present compounds include, without limitation, pyridine, N,N-dimethylaminopyridine, diazabicyclononane, diazabicycloundecene, N-methyl-N-ethylamine, diethylamine, triethylamine, diisopropylethylamine, mono-, bis- or tris-(2-hydroxyethyl)

amine, 2-hydroxy-tert-butylamine, tris(hydroxymethyl) methylamine, N,N-dimethyl-N-(2-hydroxyethyl)amine, tri-(2-hydroxyethyl)amine and N-methyl-D-glucamine. For additional examples of "pharmacologically acceptable salts," see Berge et al., *J. Pharm. Sci.* 66:1 (1977).

Compounds disclosed herein can be crystallized and can be provided in a single crystalline form or as a combination of different crystal polymorphs. As such, the compounds can be provided in one or more physical form, such as different crystal forms, crystalline, liquid crystalline or non-crystalline (amorphous) forms. Such different physical forms of the compounds can be prepared using, for example different solvents or different mixtures of solvents for recrystallization. Alternatively or additionally, different polymorphs can be prepared, for example, by performing recrystallizations at different temperatures and/or by altering cooling rates during recrystallization. The presence of polymorphs can be determined by X-ray crystallography, or in some cases by another spectroscopic technique, such as solid phase NMR spectroscopy, IR spectroscopy, or by differential scanning calorimetry.

The pharmaceutical compositions can be administered to subjects by a variety of mucosal administration modes, including by oral, rectal, intranasal, intrapulmonary, or transdermal delivery, or by topical delivery to other surfaces. Optionally, the compositions can be administered by non-mucosal routes, including by intramuscular, subcutaneous, intravenous, intra-arterial, intra-articular, intraperitoneal, intrathecal, intracerebroventricular, or parenteral routes. In other alternative embodiments, the compound can be administered ex vivo by direct exposure to cells, tissues or organs originating from a subject.

Injectable solutions or suspensions may also be formulated, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid. Solutions or suspensions used for parenteral, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerine, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers.

The compounds can be administered parenterally, for example, by IV, IM, depo-IM, SC, or depo-SC. When administered parenterally, a therapeutically effective amount of about 0.1 to about 500 mg/day (such as about 1 mg/day to about 100 mg/day, or about 5 mg/day to about 50 mg/day) may be delivered. When a depot formulation is used for injection once a month or once every two weeks, the dose may be about 0.1 mg/day to about 100 mg/day, or a monthly dose of from about 3 mg to about 3000 mg.

The compounds can also be administered sublingually. When given sublingually, the compounds should be given one to four times daily in the amounts described above for IM administration.

The compounds can also be administered intranasally. When given by this route, the appropriate dosage forms are a nasal spray or dry powder. The dosage of the compounds for intranasal administration is the amount described above for IM administration. When administered by nasal aerosol or inhalation, these compositions may be prepared according to techniques well known in the art of pharmaceutical formulation and may be prepared as solutions in saline, employing benzyl alcohol or other suitable preservatives, absorption promoters to enhance bioavailability, fluorocarbons, and/or other solubilizing or dispersing agents.

The compounds can be administered intrathecally. When given by this route, the appropriate dosage form can be a parenteral dosage form. The dosage of the compounds for intrathecal administration is the amount described above for IM administration.

The compounds can be administered topically. When given by this route, the appropriate dosage form is a cream, ointment, or patch. When administered topically, an illustrative dosage is from about 0.5 mg/day to about 200 mg/day. Because the amount that can be delivered by a patch is limited, two or more patches may be used.

The compounds can be administered rectally by suppository. When administered by suppository, an illustrative therapeutically effective amount may range from about 0.5 mg to about 500 mg. When rectally administered in the form of suppositories, these compositions may be prepared by mixing the drug with a suitable non-irritating excipient, such as cocoa butter, synthetic glyceride esters of polyethylene glycols, which are solid at ordinary temperatures, but liquefy and/or dissolve in the rectal cavity to release the drug.

To formulate the pharmaceutical compositions, the compound can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80 or Miglyol 812), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The compound can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, polylactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The compound can be combined with the base or vehicle according to a variety of methods, and release of the compound can be by diffusion, disintegration of the vehicle, or associated formation of water channels. In some circumstances, the compound is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the compound can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the compound can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages A number of these are known in the art to be biodegradable and to lead to degradation products having no or low toxicity. Exemplary polymers include polyglycolic acids and polylactic acids, poly (DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly (epsilon-caprolactone), poly(epsilon-aprolactone-CO-lactic acid), poly(epsilon.-aprolactone-CO-glycolic acid), poly (beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

In some examples, about 0.1 mg to 1000 mg of a disclosed compound, a mixture of such compounds, or a physiologically acceptable salt or ester thereof, is compounded with a physiologically acceptable vehicle, carrier, excipient, binder, preservative, stabilizer, flavor, etc., in a unit dosage form. The amount of active substance in those compositions or preparations is such that a suitable dosage in the range indicated is obtained. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient. In some examples, the compositions are formulated in a unit dosage form, each dosage containing from about 1 mg to about 1000 mg (for example, about 2 mg to about 500 mg, about 5 mg to 50 mg, about 10 mg to 100 mg, or about 25 mg to 75 mg) of the one or more compounds. In other examples, the unit dosage form includes about 0.1 mg, about 1 mg, about 5 mg, about 10 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 400 mg, about 500 mg, about 600 mg, about 700 mg, about 800 mg, about 900 mg, about 1000 mg, or more of the disclosed compound(s). The pharmaceutical compositions may be in a dosage unit form such as an injectable fluid, an oral delivery fluid (e.g., a solution or suspension), a nasal delivery fluid (e.g., for delivery as an aerosol or vapor), a semisolid form (e.g., a topical cream), or a solid form such as powder, pill, tablet, or capsule forms.

The pharmaceutical compositions of the disclosure typically are sterile and stable under sterile conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the compound can be delivered to a subject in a manner consistent with conventional methodologies associated with management of the disorder for which treatment or prevention is sought. In accordance with the disclosure herein, a prophylactically or therapeutically effective amount of the compound and/or other biologically active agent is administered to a subject in need of such treatment for a time and under conditions sufficient to prevent, inhibit, and/or ameliorate a selected disease or condition or one or more symptom(s) thereof.

The administration of the compound of the disclosure can be for either prophylactic or therapeutic purpose. When provided prophylactically, the compound is provided in advance of any symptom. The prophylactic administration of the compound serves to prevent or ameliorate any subsequent disease process. When provided therapeutically, the compound is provided at (or shortly after) the onset of a symptom of disease or infection.

For prophylactic and therapeutic purposes, the compound can be administered to the subject by the oral route or in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, dog, sheep, porcine, feline, non-human primate, and other accepted animal model subjects known in the art. Alternatively, effective dosages can be determined using in vitro models. Using such models, only ordinary calculations and adjustments are required to determine an appropriate concentration and dose to administer a therapeutically effective amount of the compound (for example, amounts that are effective to alleviate one or more symptoms of a targeted disease). In alternative embodiments, an effective amount or effective dose of the compound may simply inhibit or enhance one or more selected biological activities correlated with a disease or condition, as set forth herein, for either therapeutic or diagnostic purposes.

The actual dosage of the compound will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the compound for eliciting the desired activity or biological response in the subject. Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects. A non-limiting range for a therapeutically effective amount of a compound and/or other biologically active agent within the methods and formulations of the disclosure is about 0.25 mg/kg body weight to about 250 mg/kg body weight, such as about 1.0 mg/kg to about 100 mg/kg body weight, or about 5 mg/kg to about 50 mg/kg body weight.

Dosage can be varied by the attending clinician to maintain a desired concentration at a target site (for example, the lungs or systemic circulation). Higher or lower concentrations can be selected based on the mode of delivery, for example, trans-epidermal, rectal, oral, pulmonary, intraosseous, or intranasal delivery versus intravenous or subcutaneous or intramuscular delivery. Dosage can also be adjusted based on the release rate of the administered formulation, for example, of an intrapulmonary spray versus powder, sustained release oral versus injected particulate or transdermal delivery formulations, and so forth.

The instant disclosure also includes kits, packages and multi-container units containing the herein described pharmaceutical compositions, active ingredients, and/or means for administering the same for use in the prevention and treatment of diseases and other conditions in mammalian subjects. Kits for diagnostic use are also provided. In one embodiment, these kits include a container or formulation that contains one or more of the compounds described herein. In one example, this component is formulated in a pharmaceutical preparation for delivery to a subject. The compound is optionally contained in a bulk dispensing container or unit or multi-unit dosage form. Optional dispensing means can be provided, for example a pulmonary or intranasal spray applicator. Packaging materials optionally include a label or instruction indicating for what treatment purposes and/or in what manner the pharmaceutical agent packaged therewith can be used.

EXAMPLES

1. Preparation of Diester in Chromone Series (1-3) and (1-8) as Starting Materials The preparation of the starting substrate (1-3) in chromone series necessary for the application of the domino strategy to the synthesis of various pyridone type compounds is highlighted in Scheme 1.

Even if 3-formylchromone (1-2) is commercial, we were able to prepare it easily in large scale in agreement with the protocol already reported in literature. Thus this substrate was obtained with a very good yield (92%) from ortho-hydroxy-acetophenone (1-1) in the presence of DMF and POCl$_3$ according to a Vilsmeier-Hack's type reaction. Once the formyl derivative (1-2) obtained, it underwent a condensation reaction with diethyl malonate by using acetic anhydride and K$_2$CO$_3$ as base under heating, to provide finally the expected diester of 3-formylchromone (1-3) with an almost quantitative yield (>95%).

Scheme 1.

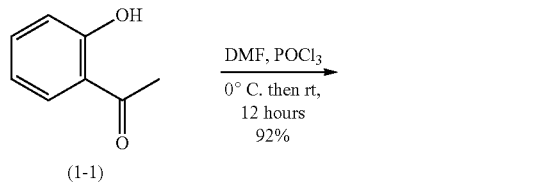

In the same way, another substrate bearing a benzyloxy group on the aromatic nuclei of the chromone (1-8) was synthesized in an effective two step-sequence procedure starting from the commercially available 2,5-dihydroxyacetophenone (1-4). Firstly, a double formylation reaction of the latter compound by Vilsmeier-Haack type reaction provides 6-hydroxy-3-formylchromone (1-5) in 77% yield. This intermediate, after O-alkylation reaction according to the conditions often used in our laboratory, furnished after 14 hours of reflux in dry toluene, the benzyloxy derivative (1-7) in 55% yield after purification (Scheme 2).

Scheme 2.

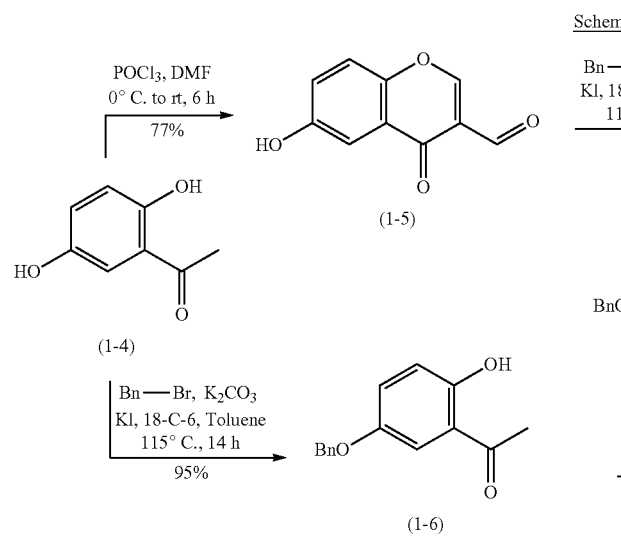

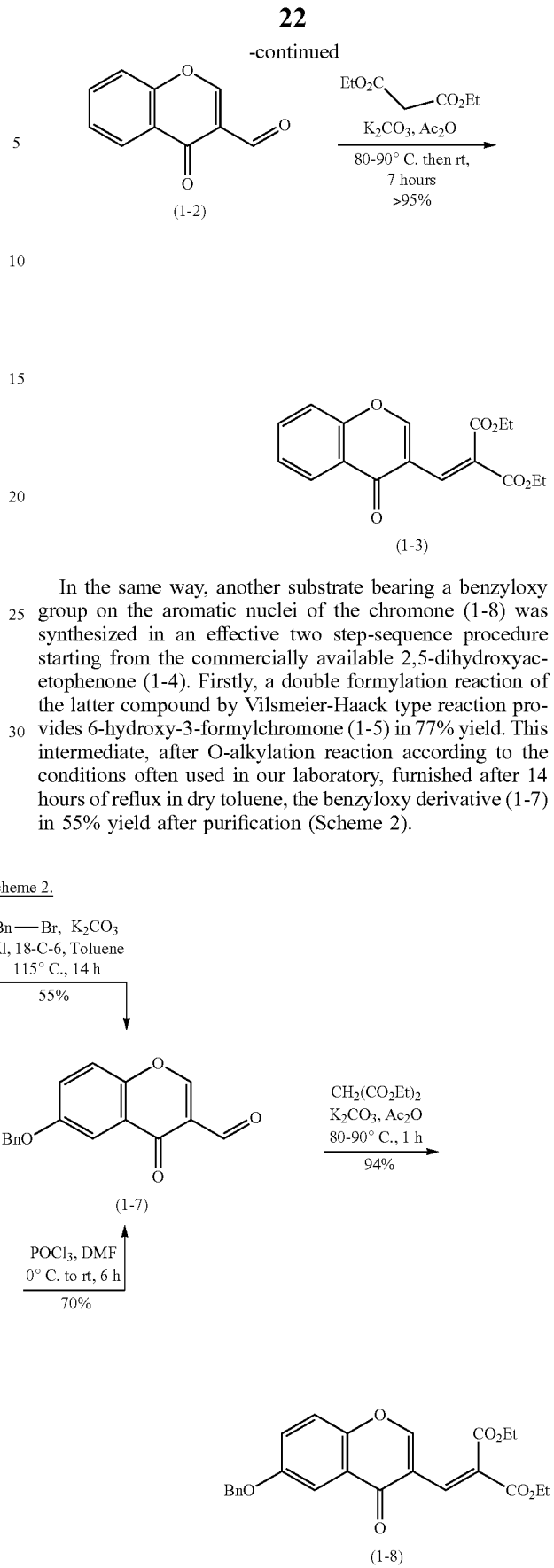

The second alternate way consists in making at first the protection of the OH function with a benzylic group by involving the same conditions as for the previous O-alkylation reaction to furnish the acetophenone derivative (1-6) in a very good yield (95%). To form the product (1-7), beforehand synthesized by the other methodology, acetophenone derivative (1-6) was submitted to Vilsmeier-Haack reaction using standard conditions (70%). Knoevenagel condensation of the resulting product (1-7) with diethyl malonate provided in an ultimate stage the expected diester (1-8) in high yield (94%).

In view of these results (Scheme 2), we can notice that in priori both ways can be used to synthesize the intermediate (1-7) in an overall yield of 42% and 66%, respectively, from the dihydroxy-acetophenone (1-4) as the raw material; with however the second way more effective in term of yield.

2. Synthesis of 2-Pyridones Via Domino Process by Addition of Amines

At the outset, we decided to start the work with the diester chromone (1-3) which will be afterward used as model substrate in the synthesis of the targeted pyridin-2-ones. Then, another short series of pyridin-2-ones containing some examples with its analogue (1-8) will also be realized.

3). Interestingly, the use of DCM at room temperature finally turns out to be more effective and produces the expected domino product CPADML10 in 90% isolated yield.

From a mechanistic point of view, the reaction takes place in three successive stages according to a process domino. This consists on the amine nucleophile attack on substrate (1-3) according to an interesting 1,6-aza-Michäel addition to furnish an N, O-acetal intermediate unstable, which, after chroman-4-one ring opening generates an enamine intermediate in two possible instable Z and/or E stereoisomers difficult to isolate. Then, an intramolecular peptide coupling through nitrogen atom attack on a carbonyl group of the ester function, followed ultimately by the spontaneous elimination of one molecule of ethanol, leads to the expected pyridone CPADML10.

From these positive results, we then decided to use other primary amines such as alkyl-, alkylaryl- and alkylheteroarylamines with the aim of insuring a molecular diversity necessary for the biological issues. The various products obtained by using this domino process are isolated in yields ranging from 62% up to 95% and are summarized in the Table 1. As highlighted, the amines used are compatible in almost all cases except in the case of sterically hindered alkylarylamine (entry 9) or amine bearing on its aromatic system of substituent with electro-withdrawing effect (entry 11). The latter pulled, as we could expect it, a significant decreasing in the reaction yields (62-68%).

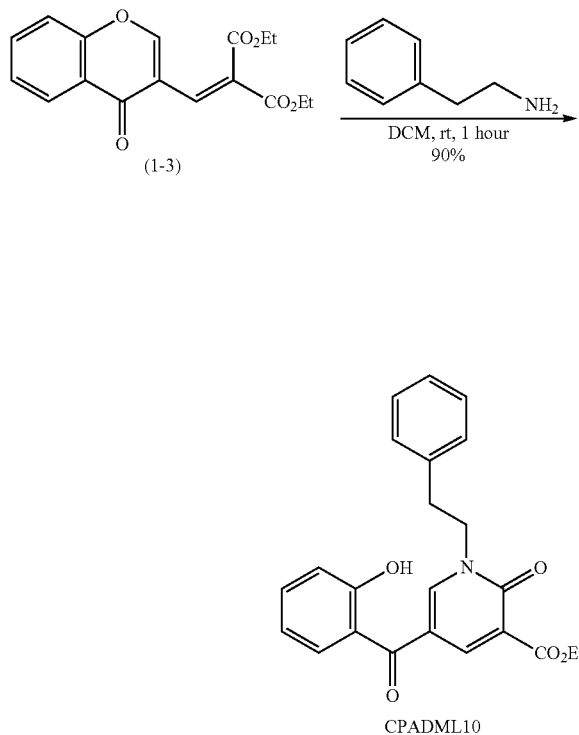

Scheme 3.

The first amine that we chose for the reaction screening without base and heating was phenylethylamine. Several solvents (ethanol, diethyl ether, dichloromethane, THF, toluene, etc. . . . ) were tested at first at room temperature. From all conditions tested, it seemed that only one hour of the reaction is needed for the formation the pyridine CPADML10 in yield superior to 70% in every case (Scheme

TABLE 1

Obtention of N-substituted pyridin-2-ones CPADML1-6,8-11,14,18*

| Entry | $R^1$ | R—$NH_2$ | Yield (%) | Product |
|---|---|---|---|---|
| 1. | H | allyl-$NH_2$ | 90 | CPADML1 |
| 2. | H | $(CH_2)_8$-$NH_2$ | 65 | CPADML2 |
| 3. | H | furfuryl-$NH_2$ | 95 | CPADML3 |
| 4. | H | thienylmethyl-$NH_2$ | 80 | CPADML4 |

TABLE 1-continued

Obtention of N-substituted pyridin-2-ones CPADML1-6,8-11,14,18*

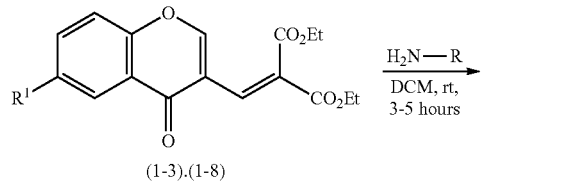

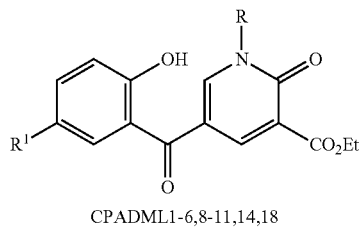

CPADML1-6,8-11,14,18

| Entry | R¹ | R—NH₂ | Yield (%) | Product |
|---|---|---|---|---|
| 5. | H | 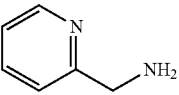 | 70 | CPADML5 |
| 6. | H | 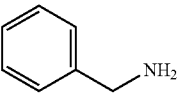 | 95 | CPADML6 |
| 8. | H | 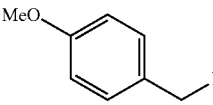 | 89 | CPADML8 |
| 9. | H | 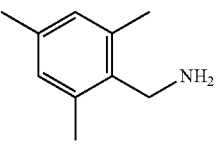 | 68 | CPADML9 |
| 10. | H | 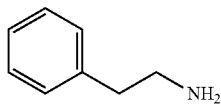 | 92 | CPADML10 |

TABLE 1-continued

Obtention of N-substituted pyridin-2-ones CPADML1-6,8-11,14,18*

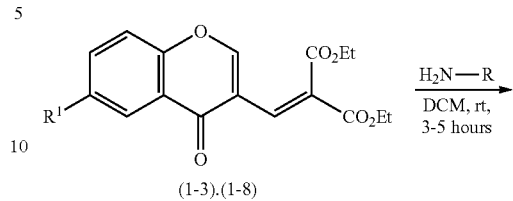

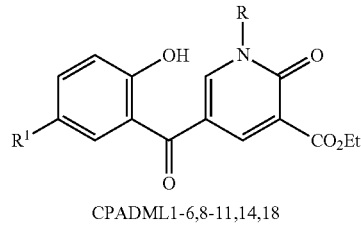

CPADML1-6,8-11,14,18

| Entry | R¹ | R—NH₂ | Yield (%) | Product |
|---|---|---|---|---|
| 11. | H | 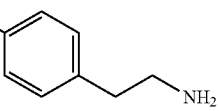 | 62 | CPADML11 |
| 14. | H | 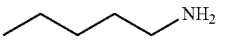 | 94 | CPADML14 |
| 18. | OBn |  | 79 | CPADML18 |

*The yields were reported for the isolated products after separation by silica gel column chromatography.

One of the first examples reported in the literature in this domain is described by Ghosh et al. This involves a panel of α,β-unsaturated compounds, obtained according to a condensation reaction between 3-formylchromone and reagents such as malonates, malononitriles or keto-esters, with nucleophiles like hydrazines, hydroxylamine and p-toluidine. The unique pyridone obtained in the latter case, and related to our CPADML derivatives, was isolated in only 25% yield without any explanation and complete product characterization.

In another stage we explored the domino process by using other amines containing an halogen atom such as 2-bromobenzylamine and an heterocyclic ring such as tryptamine (Scheme 4) starting from the ester chromone (1-3). In the case of 2-bromobenzylamine as nucleophile, the reaction after 3 hours, provide the expected domino product CPADML7 in good yield (87%) accompanied, however, with another compound (1-9) in only 5% yield. Until now, the obtention of this type of secondary 'or intermediate' product was never described in the literature. This one was never evoked either during addition of amines onto α,β-unsaturated diesters of the chromone nuclei described above (Table 1). Besides the structural determination of enaminodiester (1-9) by NMR studies, the structure was secured by X-Ray analysis confirming thus the Z stereochemistry of the exocyclic olefin part of the chroman-4-one heterocycle.

Scheme 4

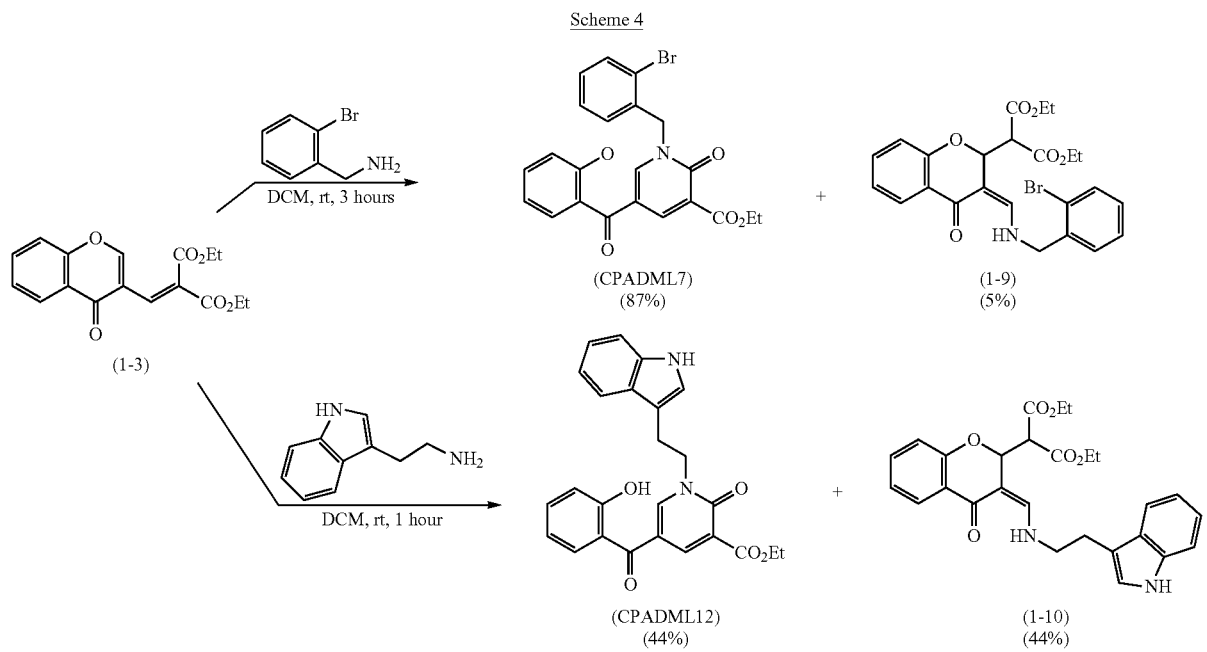

With the tryptamine as co-reactant, the reaction in DCM at room temperature provides after one hour the 2-pyridone CPADML12 in only 44% yield separable from the mixture by chromatography on silica gel column. This was also accompanied with another compound identified to be the enaminodiester (1-10) similar to (1-9) in also same 44% yield.

In the next part, we dedicated to optimize the reaction conditions to deliver selectively the pyridone product CPADML12 or the enaminodister (1-10) by studying the impact of the reaction temperature, the nature of the catalyst as well as his charge in DCM as solvent.

TABLE 2

Screening of the addition reaction of tryptamine onto the diester (1-3)

| Entry | Catalyst (mol %) | Total yield (%) rt. | Total yield (%) 40° C. | Ratio (1-10):(CPADML12) rt. | Ratio (1-10):(CPADML12) 40° C. |
|---|---|---|---|---|---|
| 1. | No catalyst | 88 | 98 | 1:1 | 3:3 |
| 2. | ZnCl$_2$(10) | 80 | 89 | 4:5 | 1:2 |
| 3. | CuI(10) | 78 | 82 | 3:4 | 1:2 |
| 4. | CsF(5) | 93 | NR* | 0:1 | NR |
| 5. | LiClO$_4$(10) | 82 | 93 | 1:2 | 3:7 |
| 6. | Bi(OTf)$_3$(5) | 88 | 90 | 1:4 | 1:4 |
| 7. | Ti(OiPr)$_4$(10) | 85 | 96 | 1:4 | 0:1 |
| 8. | TFA(10) | 70 | NR | 0:1 | NR |

*The reaction was not realized.

In this part dedicated to the screening of the reaction temperature, two reaction temperatures were chosen, room temperature and 40° C. As shown, reflux in DCM (40° C.) seems to be more efficient in term of the reaction yield in all attempts (Table 2).

As we can observe in Table 2, by comparison with the reaction without catalyst (entry 1), the use at room temperature of 10 mol % of ZnCl$_2$ (entry 2) of CuI (entry 3) resulted in the formation of both compounds (1-10):(CPADML12) in ratio of 4:5 and 3:4, respectively, with a weak improvement. More encouraging reaction profiles were obtained on the other hand in the cases of LiClO$_4$ (entry 5), Bi(OTf)$_3$(entry 6) and Ti(OiPr)$_4$ (entry 7). In these cases, the reaction proceeded with good yields and the products (1-10): (CPADML12) ratios are superior to 1:2 in favor of the pyridone system CPADML12. CsF and TFA (entries 4 and 8) were the most effective for the exclusive obtaining of the pyridone CPADML12 after 30 min of reaction at room temperature. In the case of the CsF, the expected compound (CPADML12) was isolated after precipitation in a very good yield (93%) after a simple washing with cold diethyl ether. In the case of TFA, the neutralization with NaHCO$_3$, the extraction with DCM of the reaction mixture followed by the evaporation of the solvent were necessary to obtain the expected product (CPADML12) in only 70% yield.

Once the reaction temperature of the catalyzed reactions was increased to 40° C. (gentle reflux of DCM), the formation of the pyridone (CPADML12) becomes the majority in every case with ratios higher than at room temperature, excepted the reaction with Bi(OTf)$_3$ which deliver the products (1-10):(CPADML12) in the same ratio of 1:4 (entry 6). Another remarkable result was also obtained with Ti(OiPr)$_4$ as catalyst. In this case, the pyridone (CPADML12) as the exclusive product was isolated with an excellent 96% yield (entry 7).

From these results, we can conclude that in every case where catalysts and/or heating up to 40° C. were used, the selectivity of the reaction for the formation of the expected 2-pyridone is appreciably improved. In this sense, when the best conditions with CsF (entry 4) were applied to chromone substrate (1-3) and 2-bromobenzylamine in DCM, the reaction deliver exclusively the pyridone product CPADML7 in high yield (95% instead of 87%) without no traces of the enamino-chromanone (1-9), thus validating these optimized conditions.

Another simple approach was also envisioned for the synthesis of N-substituted 2-pyridones. This consists on a direct alkylation reaction of the pyridone N-free substrates at the level of the nitrogen atom of the pyridine nuclei. For that purpose, a first stage was dedicated to the synthesis of the starting substrate (1-11) (Scheme 5) in addition to CPADML17 with benzyloxy substituent.

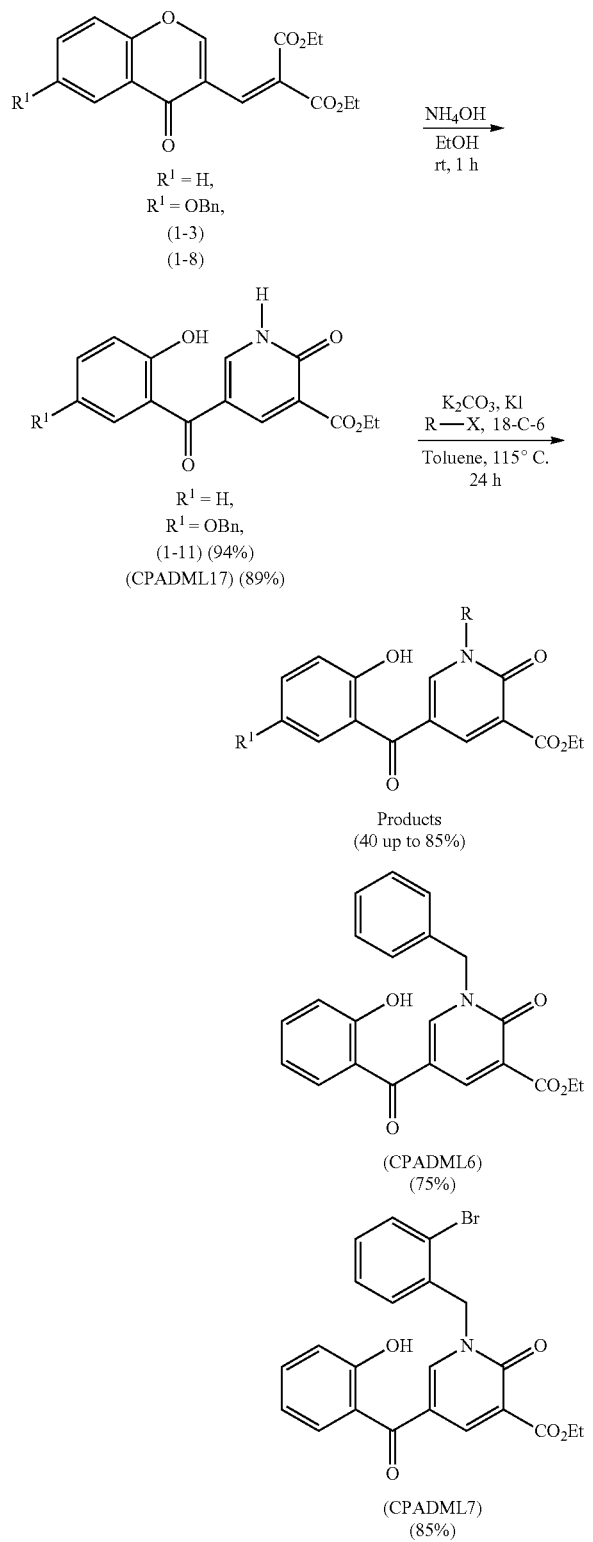

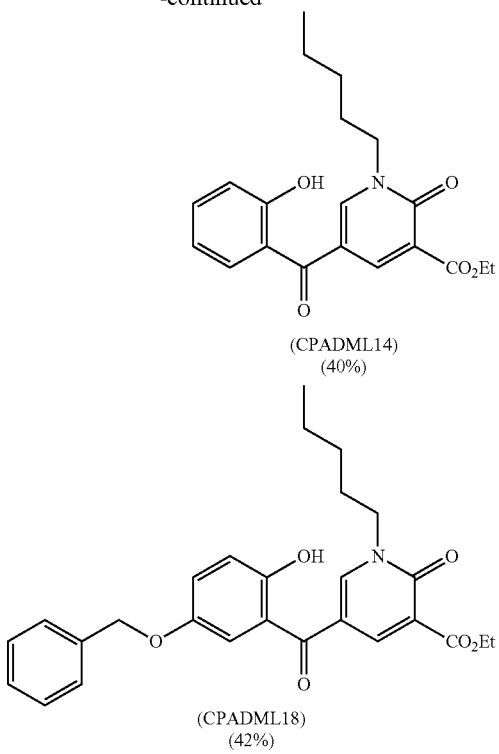

Typically, a solution containing two equivalents of ammonium hydroxide was brought together with diesters (1-3) or (1-8) dissolved in ethanol. After one hour of the reaction at room temperature, the N-free pyridones (1-11) and (CPADML17) were isolated as the sole reaction products in 94% and 89% yields, respectively.

Afterward, the N-alkylation reactions were made in phase transfer catalysis (PTC) conditions by using RX as electrophilic substrate, $K_2CO_3$ as base and a mixture of KI and (18-C-6) as catalyst in the toluene at reflux. As 2-pyridones can exist also under their two tautomer forms in equilibrium (2-Pyridone⇌hydroxypyridine), several authors have studied the selectivity of the N- vs. O-alkylation reaction by varying numerous parameters such as the temperature, the solvent, the base, the alkylating agents and the substituents on the pyridine/pyridone skeleton. From these studies, it appears that the presence of electro-withdrawing group at the ortho- and/or para-position of the 2-oxo group of the azaheterocycle is favorable for the total N-alkylation process. This fact is also confirmed by our studies as shown in Scheme 5.

3. Synthesis of O-Substituted 2-Pyridones

During these works concerning the synthesis of a short library of 2-pyridones, we decided to realize anther series of compounds, but this time containing 2-pyridones substituted at the level of the oxygen atom of hydroxy-benzoyle fragment present in certain 2-pyridones obtained above. The results of the investigations we done in this context are summarized in Table 2.

TABLE 3

O-alkylation reaction of OH phenolic of the pyridine system

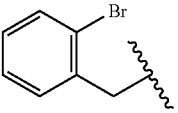 [SMILES: *Cc1ccccc1Br]

| Entry | R | R[1] | R[2]—X | Time (h) | Yield (%) | Product |
|---|---|---|---|---|---|---|
| 1. | 2-bromobenzyl | H | CH$_3$I[a] | 24 | 92 | CPADML13 |
| 2. | n-hexyl | H | CH$_3$I[a] | 14 | 94 | CPADML15 |
| 3. | benzyl | H | n-pentyl-Br[b] | 18 | 98 | CPADML16 |

[a]Two equivalents of CH$_3$I were used and the reaction was heated at 40° C. for 2 h.
[b]Twe equivalents of n-pentyl bromide were used.

Under the PTC conditions used as for the N-alkylation reaction discussed above, the expected O-alkylation products CPADML13, CPADML15 and CPADML16 were obtained easily and cleanly in very high yields (92-98%) (Table 3, entries 1-3).

4. Hydrolysis of the Ester Function for 2-Pyridones

To continue in the diversification of our pyridone platform, hydrolysis of the ester function was envisaged. For this purpose, the synthesis of carboxylic acids was realized by hydrolysis in acidic medium (Table 4).

TABLE 4

Hydrolysis of the ester function of 2-pyridones

| Entry | Reactant | R | $R^1$ | $R^2$ | Product | Yield (%) |
|---|---|---|---|---|---|---|
| 1. | 1-11 | H | H | H | CPADML19 | 90 |
| 2. | CPADML6 | benzyl (CH$_2$Ph) | H | H | CPADML20 | 93 |
| 3. | CPADML14 | n-pentyl | H | H | CPADML21 | 83 |

After a large screening of the hydrolyze conditions, we have found that treatment of ester derivative with a mixture of HCl/Ac$_2$O in 1:3 ratio at 90° C. for 2-3 hours followed by cooling of the reaction mixture at room temperature constitutes the best formation to deliver the expected carboxylic acids. Interestingly, neither 0-free and/or N-free do not have a fatal impact on the hydrolysis reaction of the ester derivatives. Under these conditions, acids CPADML19, CPADML20 and CPADML21 were isolated cleanly as crystalline materials in very good yields (Table 4) by simple filtration on section.

Experimental Part

General Remarks

Unless otherwise specified, the chemical compounds were purchased from commercial suppliers (Aldrich, Acros, Alfa, etc. . . . ) and used without further purification.

The reactions were carried out in standard dry glassware under argon atmosphere or in sealed tube in some cases where organometallic reagents were involved.

All solvents were distilled prior to use. THF was distilled from sodium and benzophenone. DMF, toluene and dichloromethane were distilled from calcium hydride and stored over molecular sieves 4 Å.

$^1$H and $^{13}$C NMR spectroscopic data were recorded on a Bruker Advance 300 spectrometer at room temperature at 300 MHz and 75 MHz respectively by using broadband proton decoupling for $^{13}$C NMR. All spectra were calibrated using the residual solvent peaks as references: 7.26 and 77.00 ppm for CDCl$_3$ or 2.50 and 39.50 respectively for DMSO-d$_6$.

For $^1$H NMR data, the multiplicities are reported using the following abbreviations: s (singlet), d (doublet), t (triplet), q (quartet), m (multiplet), bs (broad singlet) or a suitable combination. The coupling constants (J) are displayed in ppm relative to tetramethylsilane as an internal standard. The assignments of proton resonances were based on $^1$H NMR, $^1$H COSY, HMQC and HMBC analysis.

The separation or purification on milligram scale for crude products and the advancement of reactions were monitored by thin-layer chromatography (TLC), which was carried out on Macherey-NagelR silica gel 60 F$_{254}$ aluminum plates. The spots were visualized with UV light at 254 and 380 nm. The following reagents were used as staining detectors:

p-anisaldehyde: 6.4 mL of p-anisaldehyde added to a mixture of glacial acetic acid (2.6 mL) and concentrated sulfuric acid (8.4 mL) dissolved in 232 mL of ethanol;
potassium permanganate: 0.05% aqueous KMnO$_4$;
ninhydrin: 0.2 g of ninhydrin were dissolved in 100 mL of ethanol.

For flash chromatography Macherey-NagelR silica gel (40-63 μm) was used and the elution was performed generally with a mixture of cyclohexane/ethyl acetate system.

High resolution mass spectra (HRMS) were recorded on a 6530 Q-TOF (Agilent System) apparatus and the electrospray ionization (ESI)-MS was measured in positive or negative ionization mode (ESI$^±$) by using an Agilent Jet Stream or APCI pump: precision >1 ppm, resolution (M/Z=118)>10,000 and resolution (M/Z=1522)>26,000.

The melting points were taken in open capillary, recorded on a Stuart Scientific analyzer SMP 10 apparatus and are uncorrected.

Infrared (IR) spectra were performed as neat on Perkin Elmer FT-IR spectrophotometer.

For the cited compounds, only broad and strong signals are reported (wavenumbers, cm$^{-1}$).

1. General Procedures (GPs)
GP1: Chromones Synthesis

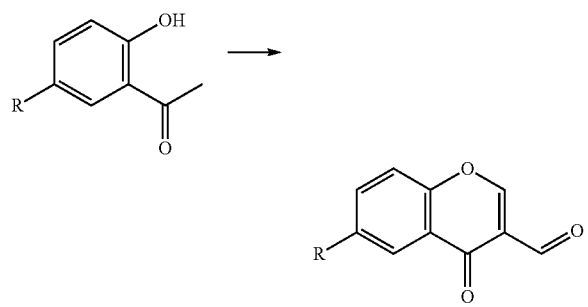

The 3-formylchromones used as starting materials were prepared by an improved method according to Nohara's procedure. Over an ice bath containing a stirred solution of appropriate 2-hydroxyacetophenones in DMF, the $POCl_3$ (5 equiv.) was added slowly through a dropping funnel and stirring was continued at 0° C. until no gas emission were observed. Then the mixture was kept at room temperature until the starting material had been completely consumed (TLC analysis).

The reaction was hydrolyzed by pouring it into crushed ice. After stirring for few minutes, the formed precipitate was filtered, washed with water and dried to yield pure desired chromones.

GP2: Chromone Esters Derivatives Synthesis

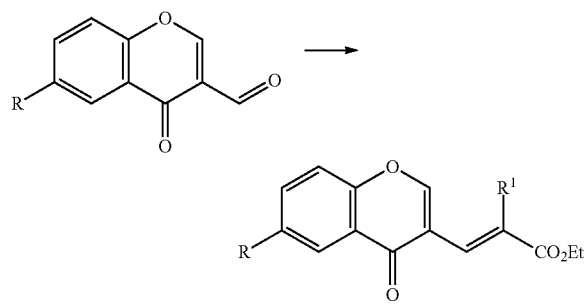

The chromone diester derivatives ($R^1$=$CO_2Et$) were prepared by an improved method according to Ghosh's procedure. To a previously heated solution of appropriate 3-formylchromone in acetic anhydride, the $K_2CO_3$ (0.1 equiv.) and diethyl malonate (1.5 equiv.) were added and the mixture was heated at 90° C. until no starting material was observed (TLC analysis). After cooling, diethyl ether was added and the reaction mixture was stirred at room temperature for few hours. Then the precipitate thus formed was filtered and washed with cyclohexane to afford the corresponding diesters.

The chromone monoester derivative (R and $R^1$ =H) was prepared following the Bodwell procedure. To a previously stirred solution of THF containing triethyl phosphonoacetate (1.3 equiv.) in presence of NaH 60% in mineral oil (2 equiv.), a solution of 3-formylchromone (1 equiv.) in THF, was slowly added and the resulting orange mixture stirred at room temperature for 12 hours. Then the mixture was quenched with a saturated solution of $NH_4Cl$ and stirring was continued for 30 minutes.

The solvent was evaporated under reduced pressure and to a reaction mixture were added water and dichloromethane. The layers were separated again and the product extracted from with dichloromethane. Then the resulting organic layers were combined and the solvent evaporated under reduced pressure. The solid obtained after was recrystallized from ethanol, filtered and washed with cold diethyl ether to obtain the desired chromone monoester derivative.

GP3: Domino Process

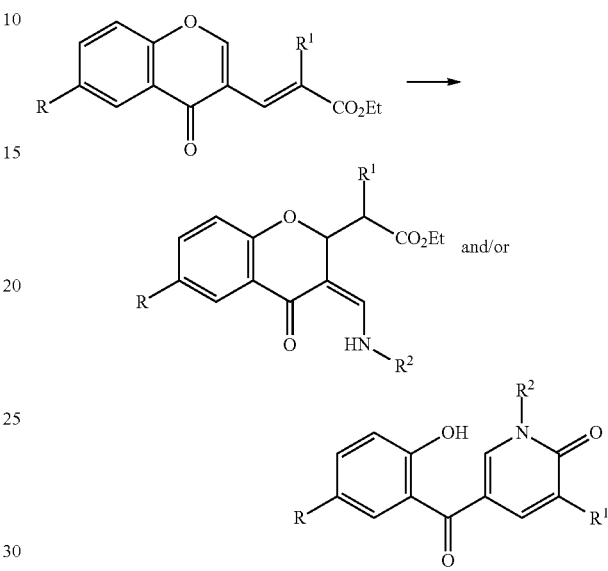

Enaminochromanones and pyridin-2-ones were synthesized according 3 similar procedures:

To a solution of appropriate chromone ester derivatives in dichloromethane or ethanol, the amine (1.1 equiv.) was added dropwise. The reaction mixture was stirred at room temperature and the consumption of substrate was followed by TLC. In some cases, after full conversion of ester derivatives, the final product precipitated and the solid was filtered and washed with cold diethyl ether or cyclohexane to yield pure pyridin-2-ones. In other situations the solvent was evaporated under reduced pressure and the resulting residue was purified by chromatography on silica gel column (eluted with 100% to 0% cyclohexane in EtOAc) to yield pyridin-2-ones and/or enaminochromanones.

To a previously stirred solution of appropriate chromone ester derivatives in presence of CsF (catalytic) in dichloromethane, the amine (1.1 equiv.) was added slowly. The reaction mixture was stirred at room temperature until average or full consumption of substrates was observed (TLC and/or $^1H$ NMR analysis). Depending on final product, the isolation of thus was completed by filtration of formed precipitated or by purification on silica gel column chromatography (100% to 0% cyclohexane in EtOAc elution) to yield pure pyridin-2-ones and/or enaminochromanones.

To a previously stirred solution of appropriate chromone ester derivatives in presence of CsF (catalytic) in dichloromethane, the amine (1.1 equiv.) was slowly added. The reaction mixture was then heated at 40° C. until full conversion of substrates was observed (TLC analysis).

At the end of the reaction, fast purification by silica gel column chromatography (100% to 0% cyclohexane in EtOAc) or precipitation with diethyl ether followed by filtration of solid, yielded pure pyridin-2-one compounds.

GP4: Pyridin-2-Ones Alkylation

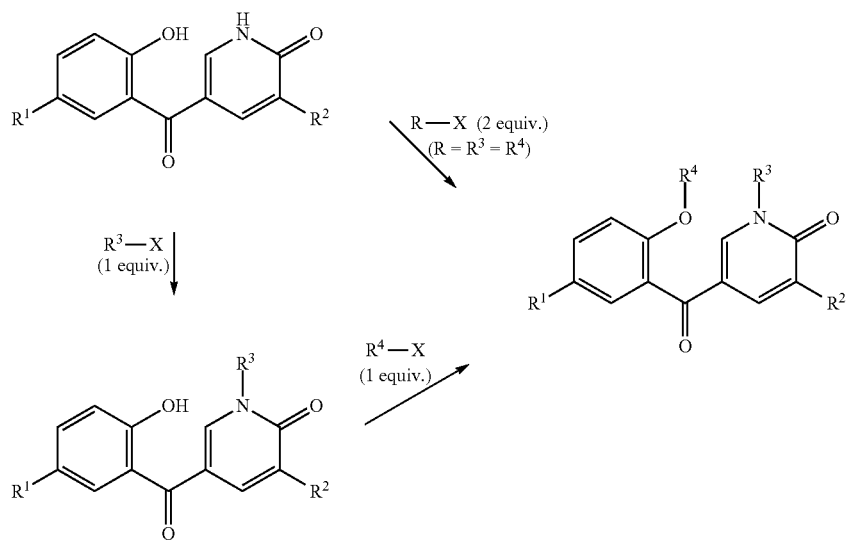

To a previously heated solution (90° C.) containing appropriated pyridin-2-ones, potassium carbonate (2.5 equiv.), potassium iodide (0.1 equiv.) and 18-crown-6 (catalytic) in toluene, the alkyl- or alkylaryl halide R—X (1-2 equiv.) was added dropwise and the mixture heated at 40° C. or 115° C. for 2 hours then left at room temperature during overnight.

After consumption of starting materials (TLC analysis) the mixture was filtered through celite and rinsed with dichloromethane. Then the organic solution was concentrated under reduced pressure and the crude product purified by chromatography on silica gel column (100% to 50% of cyclohexane in EtOAc) or the reaction mass was worked up with saturated NaHCO$_3$ solution, water and brine to yield pure O- and/or N-alkylated pyridones.

GP5: Pyridin-2-Ones Hydrolysis

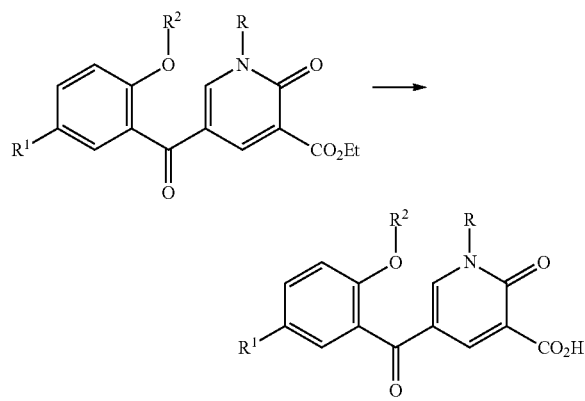

The appropriate 2-pyridone ester derivatives were solubilized in a solution containing 37% HCl in water and acetic anhydride (rapport 1:3, v/v) at room temperature and the resulting mixture heated at 90° C. for 2-3 hours. After cooling, the product precipitated and the solid was filtered washed with water and dried to yield pure pyridone acid derivatives.

2. Structural Formulas and Characterization of Synthesized Compounds

3-Formylchromone (1-2)

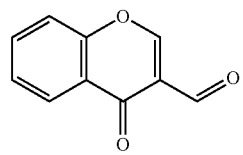 [SMILES: O=Cc1coc2ccccc2c1=O]

Synthesized according to (GP1) by using the commercially available 2-hydroxyacetophenone (1-1) (5.00 g, 36.7 mmol) in dry DMF (50 mL) and POCl$_3$ (28.14 g, 183.5 mmol) at 0° C. and room temperature during overnight. Standard hydrolysis followed by filtration afforded the compound (1-2) (5.88 g, 92% yield) as white solid; (mp 151-153° C., 150-154° C.).

$^1$H NMR (300 MHz, CDCl$_3$) $\delta_H$ (ppm) 7.45-7.60 (m 2H); 7.76 (t, J=7.8 Hz, 1H), 8.31 (d, J=8.0 Hz, 1H), 8.56 (s, 1H, OCH), 10.40 (s, 1H, CHO).

Physical and $^1$H NMR spectral data are in accordance with those previously reported. Diethyl 2-[(4-oxo-4H-chromen-3-yl)methylene]malonate (1-3)

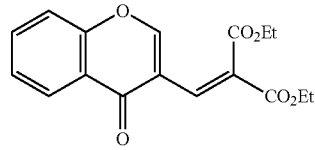 [SMILES: CCOC(=O)C(=Cc1coc2ccccc2c1=O)C(=O)OCC]

Synthesized according to (GP2A) by using the chromone (1-2) (5.00 g, 28.7 mmol), K$_2$CO$_3$ (0.4 g, 2.87 mmol) and diethyl malonate (6.90 g, 43.10 mmol) in acetic anhydride (21 mL) at 90° C. during 3 hours then diethyl ether (50 mL) was added and the solution was stirred at room temperature during overnight. The formed precipitate was filtered and rinsed with cyclohexane to yield the diester (1-3) (8.81 g, 97% yield) as white powder; (mp 112-114° C., Lit. 111° C.).

$^1$H NMR (300 MHz, CDCl$_3$): $\delta_H$ (ppm) 1.28 (dt, J=15.4, 7.3 Hz, 6H, 2×CH$_3$), 4.29 (dq, J=14.2, 7.1 Hz, 4H, 2×OCH$_2$), 7.41 (dd, J=13.0, 7.9 Hz, 2H), 7.67 (t, J=7.4 Hz, 1H), 7.73 (s, 1H, CH$_\beta$), 8.19 (d, J=7.8 Hz, 1H), 8.28 (s, 1H, OCH).

Physical and $^1$H NMR spectral data are in accordance with those previously reported.

6-Hydroxy-3-formylchromone (1-5)

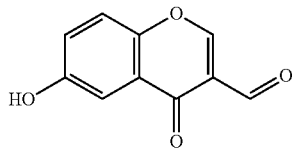

Synthesized according to (GP1) by using commercially available 2,5-dihydroxyacetophenone (1-4) (3.00 g, 19.7 mmol) in dry DMF (15 mL) and POCl$_3$ (15.12 g, 99.0 mmol) at room temperature during 4 hours. Standard hydrolysis followed by filtration afforded chromone (1-5) (3.75 g, 77% yield) as beige solid; (mp 238-240° C., 223-226° C.).

$^1$H NMR (300 MHz, DMSO-d$_6$) $\delta_H$ (ppm) 7.29 (dd, J=9.0, 3.0 Hz, 1H), 7.41 (d, J=2.9 Hz, 1H), 7.63 (d, J=9.0 Hz, 1H), 8.86 (s, 1H, OCH), 10.12 (s, 1H, OH), 10.29 (bs, 1H, CHO).

Physical and $^1$H NMR spectral data are in accordance with those previously reported.

6-Benzyloxy-3-formylchromone (1-7)

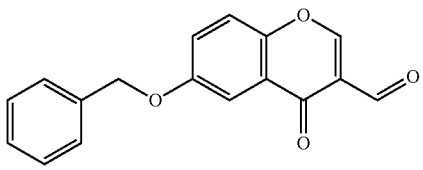 [SMILES: O=Cc1coc2ccc(OCc3ccccc3)cc2c1=O]

Synthesized according to (GP1) by using the 2-hydroxy-5-benzyloxyacetophenone (1-6) previously synthesized in 95% yield by alkylation of (1-4).

To a solution of acetophenone (1-6) (2.93 g, 12.1 mmol) in dry DMF (10 mL), POCl$_3$ (9.27 g, 60.5 mmol) was added at 0° C. After stirring at room temperature for 2 hours and standard hydrolysis followed by filtration, the chromone (1-7) (3.39 g, 70% yield) was isolated as yellow solid; (mp 157-159° C., 163-166.5° C.).

$^1$H NMR (300 MHz, CDCl$_3$) $\delta_H$ (ppm) 5.17 (s, 2H, OCH$_2$), 7.34-7.51 (m, 7H), 7.75 (d, J=2.9 Hz, 1H), 8.52 (s, 1H, OCH), 10.40 (s, 1H, CHO).

Physical and $^1$H NMR spectral data are in accordance with those previously reported.

Diethyl 2-[6-benzyloxy-(4-oxo-4H-chromen-3-yl)methylene]malonate (1-8)

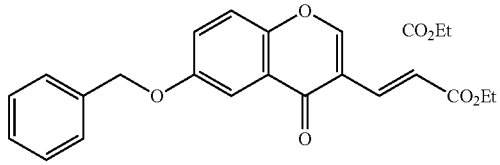 [SMILES: CCOC(=O)/C=C/c1coc2ccc(OCc3ccccc3)cc2c1=O]

Synthesized according to (GP2A) by using the 3-formylchromone (1-7) (0.20 g, 0.71 mmol), K$_2$CO$_3$ (0.01 g, 0.07 mmol) and diethyl malonate (0.17 g, 1.07 mmol) in acetic anhydride (5 mL) at 90° C. during 1 hour. Diethyl ether (10 mL) was then added and the solution stirred at room temperature during overnight. The formed precipitate was filtered off on section and rinsed with cyclohexane to yield the diester (1-8) (0.27 g, 90% yield) as yellow solid; (mp 130-132° C.).

R$_f$=0.40 (cyclohexane/EtOAc, 9:1).

IR (neat, $v_{max}$/cm$^{-1}$) 1724 (C=O, ester), 1687 (C=O, ester), 1658 (C=O, ketone), 1610 (C—O), 1483 (C—C, aromatic), 1450 (C—C, ester), 1220 (C—O, ester), 1064 (C—O, ester).

$^1$H NMR (300 MHz, CDCl$_3$): $\delta_H$ (ppm) 1.32 (dt, J=11.2, 7.1 Hz, 6H, 2×CH$_3$), 4.32 (dq, J=14.7, 7.3 Hz, 4H, 2×OCH$_2$), 5.15 (s, 2H, OCH$_2$), 7.31-7.49 (m, 7H), 7.70 (d, J=2.6 Hz, 1H), 7.78 (s, 1H, CH$_\beta$), 8.30 (s, 1H, OCH).

$^{13}$C NMR (75 MHz, CDCl$_3$): $\delta_C$ (ppm) 14.0 (CH$_3$), 14.1 (CH$_3$), 61.7 (2×OCH$_2$), 70.7 (OCH$_2$), 106.8 (CH$_{aro}$), 118.3 (C$_q$), 119.7 (CH$_{aro}$), 124.4 (C$_q$), 124.7 (CH$_{aro}$), 127.7 (2×CH$_{aro}$), 128.0 (C$_q$), 128.3 (CH$_{aro}$), 128.7 (2×CH$_{aro}$), 133.3 (CHO, 136.0 (C$_q$), 150.8 (C$_q$), 156.2 (OCH), 156.6 (C$_q$), 163.9 (C$_q$, ester), 166.0 (C$_q$, ester), 174.9 (C$_q$, ketone).

HRMS (ESI$^+$) calcd for C$_{24}$H$_{23}$O$_7$ [M+H]$^+$ 423.1444, found 423.1427.

3-Ethoxycarbonyl-5-(o-hydroxybenzoyl)-1-(allyl)pyridin-2-one (CPADML1)

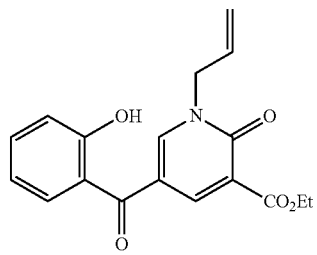 [SMILES: C=CCn1cc(C(=O)c2ccccc2O)cc(C(=O)OCC)c1=O]

Synthesized according to (GP3A) by using a mixture of diester (1-3) (0.50 g, 1.58 mmol) and allylamine (0.10 g, 1.74 mmol) in dichloromethane (5 mL) and stirring during 3 hours at room temperature. Diethyl ether (3 mL) was then added and the formed precipitate filtered and rinsed with cyclohexane to obtain pure pyridone (CPADML1) (0.47 g, 90% yield) as orange solid; (mp 86-88° C.).

R$_f$=0.28 (cyclohexane/EtOAc, 1:1).

IR (neat, $v_{max}$/cm$^{-1}$) 3444 (O—H$_{bonded}$), 3069 (=C—H, allyl), 2983 (C—H, aromatic), 1729 (C=O, ester), 1656

(C=O, amide), 1622 (C=O, ketone), 1484 (C—C, aromatic), 1338 (C—O, ester), 1265 (C—N), 1237 ($CH_2$—N).

$^1$H NMR (300 MHz, $CDCl_3$) $\delta_H$ (ppm) 1.37 (t, J=7.1 Hz, 3H, $CH_3$), 4.37 (q, J=7.1 Hz, 2H, $OCH_2$), 4.68 (d, J=6.0 Hz, 2H, $CH_2$ $_{allyl}$), 5.37 (t, J=12.7 Hz, 2H, $NCH_2$), 5.99 (ddt, J=12.2, 10.4, 6.1 Hz, 1H, $CH_{allyl}$), 6.94 (t, J=7.5 Hz, 1H), 7.07 (d, J=8.1 Hz, 1H), 7.46-7.58 (m, 2H), 8.14 (s, 1H, $NCH_{py}$), 8.51 (s, 1H, $CH_{py}$), 11.36 (s, 1H, OH).

$^{13}$C NMR (75 MHz, $CDCl_3$) $\delta_C$ (ppm) 14.2 ($CH_3$), 52.3 ($NCH_2$), 61.6 ($OCH_2$), 115.9 ($C_q$), 118.5 ($CH_2$ $_{allyl}$), 118.9 ($CH_{aro}$), 119.1 ($CH_{aro}$), 120.2 ($C_q$), 120.7 ($C_q$), 131.1 ($CH_{allyl}$), 131.4 ($CH_{aro}$), 136.5 ($CH_{aro}$), 143.7 ($NCH_{py}$), 146.0 ($CH_{py}$), 158.4 ($C_q$), 162.5 ($C_q$, amide), 164.1 ($C_q$, ester), 194.4 ($C_q$, ketone).

HRMS (ESI$^+$) calcd for $C_{18}H_{18}NO_5$ [M+H]$^+$ 328.1185, found 328.1180.

3-Ethoxycarbonyl-5-(o-hydroxybenzoyl)-1-(dodecyl)pyridin-2-one (CPADML2)

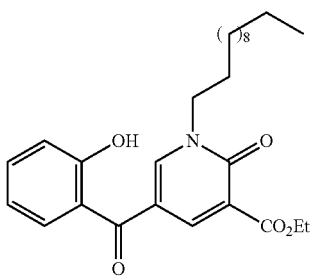

Synthesized according to (GP3A) by using a mixture of diester (1-3) (0.20 g, 0.63 mmol) and n-dodecylamine (0.13 g, 0.70 mmol) in dichloromethane (5 mL) and stirring during 5 hours. Then the solvent was evaporated under reduced pressure to yield pyridone (CPADML2) (0.19 g, 65% yield) as orange oil.

$R_f$=0.15 (cyclohexane/EtOAc, 1:1).

IR (neat, $v_{max}$/cm$^{-1}$) 2924 (C—H), 2853 ($CH_2$), 1724 (C=O, ester), 1649 (C=O, amide), 1597 (C=O, ketone), 1272 (C—O, ester), 766 (C—H, aromatic).

$^1$H NMR (300 MHz, $CDCl_3$) $\delta_H$ (ppm) 0.82 (t, J=6.5 Hz, 3H, $CH_3$ $_{dodecyl}$), 1.17-1.24 (m, 14H, 7×$CH_2$), 1.33 (t, J=7.2 Hz, 5H, $CH_3$, $CH_2$ overlapped), 1.68-1.84 (m, 2H, $CH_2$), 3.65 (q, J=7.0 Hz, 2H, $CH_2$), 4.00 (t, J=7.4 Hz, 2H, $NCH_2$), 4.32 (q, J=7.1 Hz, 2H, $OCH_2$), 6.90 (t, J=7.6 Hz, 1H), 7.03 (d, J=8.4 Hz, 1H), 7.48 (dd, J=7.4, 6.6 Hz, 2H), 8.13 (d, J=2.6 Hz, 1H, $CH_{py}$), 8.47 (d, J=2.6 Hz, 1H, $NCH_{py}$), proton from OH group was not observed.

$^{13}$C NMR (75 MHz, $CDCl_3$) $\delta_C$ (ppm) 14.1 ($CH_3$ $_{pentyl}$), 14.2 ($CH_3$), 22.6 ($CH_2$), 26.6 ($CH_2$), 29.1 ($CH_2$), 29.2 ($CH_2$), 29.3 ($CH_2$), 29.4 ($CH_2$), 29.5 ($CH_2$), 29.6 (2×$CH_2$), 31.9 ($CH_2$), 51.6 ($NCH_2$), 61.6 ($OCH_2$), 115.6 ($C_q$), 118.6 ($C_q$), 118.9 ($CH_{aro}$), 119.1 ($CH_{aro}$), 120.0 ($C_q$), 131.4 ($CH_{aro}$), 136.5 ($CH_{aro}$), 143.6 ($NCH_{py}$), 146.5 ($CH_{py}$), 158.6 ($C_q$), 162.5 ($C_q$, amide), 164.3 ($C_q$, ester), 194.5 ($C_q$, ketone).

HRMS (ESI$^+$) calcd for $C_{27}H_{38}NO_5$ [M+H]$^+$ 456.2750, found 456.2738.

3-Ethoxycarbonyl-5-(o-hydroxybenzoyl)-1-(furan-2-yl-methyl)pyridin-2-one (CPADML3)

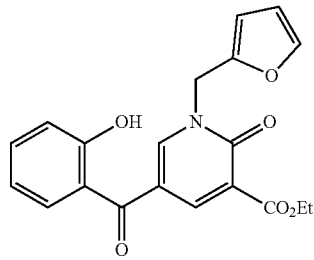 [SMILES: CCOC(=O)c1cc(C(=O)c2ccccc2O)cn(Cc2ccco2)c1=O]

Synthesized according to (GP3A) by using a mixture of diester (1-3) (0.50 g, 1.58 mmol) and furan-2-yl-methanamine (0.17 g, 1.74 mmol) in dichloromethane (5 mL) and stirring during 3 hours at room temperature. Diethyl ether (3 mL) was then added and the formed precipitate filtered and rinsed with cyclohexane to yield pyridone (CPADML3) (0.55 g, 95% yield) as yellow solid; (mp 143-145° C.).

$R_f$=0.23 (cyclohexane/EtOAc, 1:1).

IR (neat, $v_{max}$/cm$^{-1}$) 3448 (O—$H_{bonded}$), 3146 (C—H, aromatic), 3000 (C—H), 1736 (C=O, ester), 1658 (C=O, amide), 1626 (C=O, ketone), 1596 (C=C, furan) 1540 (C—C, aromatic), 1338 (C—O, ester), 1250 (C—N), 1237 ($CH_2$—N), 1151 (C—O, furan).

$^1$H NMR (300 MHz, $CDCl_3$) $\delta_H$ (ppm) 1.38 (t, J=7.1 Hz, 3H, $CH_3$), 4.38 (q, J=7.1 Hz, 2H, $OCH_2$), 5.22 (s, 2H, $NCH_2$), 6.36-6.41 (m, 1H), 6.55 (d, J=3.3 Hz, 1H), 6.92 (t, J=7.6 Hz, 1H), 7.08 (d, J=8.5 Hz, 1H), 7.43 (d, J=1.4 Hz, 1H, OCH), 7.48 (d, J=7.9 Hz, 1H), 7.53 (t, J=7.7 Hz, 1H), 8.19 (d, J=2.3 Hz, 1H, $NCH_{py}$), 8.51 (d, J=2.3 Hz 1H, $CH_{py}$), 11.38 (s, 1H, OH).

$^{13}$C NMR (75 MHz, $CDCl_3$) $\delta_C$ (ppm) 14.2 ($CH_3$), 45.6 ($NCH_2$), 61.6 ($OCH_2$), 111.1 (CH), 111.6 (CH), 115.8 ($C_q$), 118.5 ($C_q$), 118.8 ($CH_{aro}$), 119.0 ($CH_{aro}$), 120.4 ($C_q$), 131.5 ($CH_{aro}$), 136.5 ($CH_{aro}$), 143.7 (2×CH, OCH, $NCH_{py}$), 145.9 ($CH_{py}$), 147.2 ($C_q$), 158.3 ($C_q$), 162.6 ($C_q$, amide), 164.0 ($C_q$, ester), 194.3 ($C_q$, ketone).

HRMS (ESI$^+$) calcd for $C_{20}H_{18}NO_6$ [M+H]$^+$ 368.1134, found 368.1129.

3-Ethoxycarbonyl-5-(o-hydroxybenzoyl)-1-(thiophen-2-yl-methyl)pyridin-2-one (CPADML4)

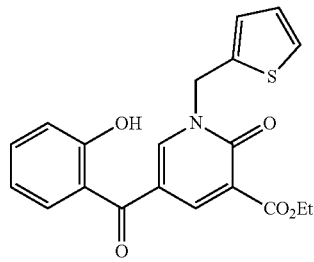 [SMILES: CCOC(=O)c1cc(C(=O)c2ccccc2O)cn(Cc2cccs2)c1=O]

Synthesized according to (GP3A) by using a mixture of diester (1-3) (0.50 g, 1.58 mmol) and thiophen-2-yl-methanamine (0.19 g, 1.74 mmol) in dichloromethane (5 mL) and stirring during 3 hours at room temperature. Diethyl ether (3 mL) was then added and the formed precipitate filtered and rinsed with cyclohexane to yield pyridone (CPADML4) (0.48 g, 80% yield) as white solid; (mp 145-147° C.).

$R_f$=0.23 (cyclohexane/EtOAc, 1:1).

IR (neat, $v_{max}$/cm$^{-1}$) 3440 (O—H$_{bonded}$), 3047 (C—H, aromatic), 3009 (C—H), 1725 (C=O, ester), 1647 (C=O, amide), 1626 (C=O, ketone), 1542 (C=C, thiophene) 1340 (C—O, ester), 1274 (C—N), 1241 (CH$_2$—N), 1140 (C—S, thiophene).

$^1$H NMR (300 MHz, CDCl$_3$) $\delta_H$ (ppm) 1.38 (t, J=7.0 Hz, 3H, CH$_3$), 4.39 (q, J=7.0 Hz, 2H, OCH$_2$), 5.38 (s, 2H, NCH$_2$), 6.89 (t, J=7.4 Hz, 1H, CH), 6.98-7.04 (m, 1H, CH), 7.06 (d, J=8.5 Hz, 1H), 7.20 (d, J=3.6 Hz, 1H, CH), 7.34 (d, J=5.2 Hz, 1H, SCH), 7.42 (d, J=8.0 Hz, 1H), 7.52 (t, J=7.8 Hz, 1H), 8.17 (d, J=1.6 Hz, 1H, NCH$_{py}$), 8.50 (s, 1H, CH$_{py}$), 11.35 (s, 1H, OH).

$^{13}$C NMR (75 MHz, CDCl$_3$) $\delta_C$ (ppm) 14.2 (CH$_3$), 47.8 (NCH$_2$), 61.6 (OCH$_2$), 116.0 (C$_q$), 118.4 (C$_q$), 118.8 (CH$_{aro}$), 119.1 (CH$_{aro}$), 120.5 (C$_q$), 127.4 (CH), 127.5 (SCH), 129.2 (CH), 131.5 (CH$_{aro}$), 135.9 (C$_q$), 136.5 (CH$_{aro}$), 143.6 (NCH$_{py}$), 145.6 (CH$_{py}$), 158.4 (C$_q$), 162.5 (C$_q$, amide), 164.0 (C$_q$, ester), 194.3 (C$_q$, ketone).

HRMS (ESI$^+$) calcd for C$_{20}$H$_{18}$NO$_5$S [M+H]$^+$ 384.0905, found 384.0930.

3-Ethoxycarbonyl-5-(o-hydroxybenzoyl)-1-(pyridin-2-yl-methyl)pyridin-2-one (CPADML5)

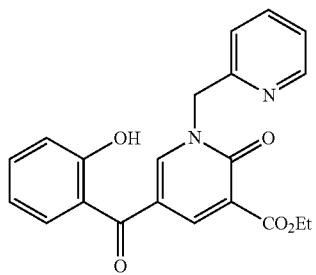 [SMILES: CCOC(=O)c1cc(C(=O)c2ccccc2O)cn(Cc2ccccn2)c1=O]

Synthesized according to (GP3A) by using a mixture of diester (1-3) (0.50 g, 1.58 mmol) and pyridin-2-yl-methanamine (0.19 g, 1.74 mmol) in dichloromethane (5 mL) and stirring during 3 hours at room temperature. Diethyl ether (3 mL) was then added and the formed precipitate filtered and rinsed with cyclohexane to yield pyridone (CPADML5) (0.42 g, 70% yield) as white solid; (mp 150-152° C.).

$R_f$=0.15 (cyclohexane/EtOAc, 1:1).

IR (neat, $v_{max}$/cm$^{-1}$) 3448 (O—H$_{bonded}$), 3065 (C—H, aromatic), 2987 (C—H), 1766 (C=O, ester), 1744 (C=O, amide), 1624 (C=N), 1595 (C=O, ketone), 1430 (C—C, aromatic), 1340 (C—O, ester).

$^1$H NMR (300 MHz, CDCl$_3$) $\delta_H$ (ppm) 1.35 (t, J=7.1 Hz, 3H, CH$_3$), 4.35 (q, J=7.1 Hz, 2H, OCH$_2$), 5.49 (s, 2H, NCH$_2$), 6.98 (t, J=7.4 Hz, 1H), 7.07 (d, J=8.3 Hz, 1H), 7.52 (dd, J=15.6, 7.4 Hz, 2H), 7.70 (d, J=7.6 Hz, 1H), 7.85 (d, J=7.0 Hz, 1H), 7.95 (t, J=7.7 Hz, 1H), 8.56 (d, J=2.3 Hz, 1H, NCH$_{py}$), 8.60 (d, J=5.0 Hz, 1H, NCH), 8.83 (d, J=2.2 Hz 1H, CH$_{py}$), 11.42 (s, 1H, OH).

$^{13}$C NMR (75 MHz, CDCl$_3$) $\delta_C$ (ppm) 14.2 (CH$_3$), 52.9 (NCH$_2$), 61.6 (OCH$_2$), 116.1 (C$_q$), 118.6 (C$_q$), 118.7 (CH$_{aro}$), 119.3 (CH$_{aro}$), 120.2 (C$_q$), 124.6 (CH$_{aro}$), 126.3 (CH$_{aro}$), 132.0 (CH$_{aro}$), 136.5 (CH$_{aro}$), 140.3 (CH$_{aro}$), 144.4 (NCH$_{py}$), 146.7 (NCH), 147.8 (CH$_{py}$), 152.0 (C$_q$), 158.8 (C$_q$), 162.5 (C$_q$, amide), 163.7 (C$_q$, ester), 194.3 (C$_q$, ketone).

HRMS (ESI$^+$) calcd for C$_{21}$H$_{19}$N$_2$O$_5$ [M+H]$^+$ 379.1294, found 379.1315.

3-Ethoxycarbonyl-5-(o-hydroxybenzoyl)-1-(benzyl)pyridin-2-one (CPADML6)

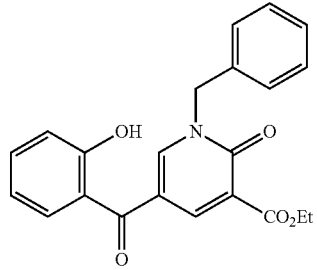 [SMILES: CCOC(=O)c1cc(C(=O)c2ccccc2O)cn(Cc2ccccc2)c1=O]

Synthesized according to (GP3A) by using a mixture of diester (1-3) (0.50 g, 1.58 mmol) and allylamine (0.19 g, 1.74 mmol) in dichloromethane (5 mL) and stirring during 3 hours at room temperature. Diethyl ether (3 mL) was then added and the formed precipitate filtered and rinsed with cyclohexane to yield the pure pyridone (CPADML6) (0.57 g, 95% yield) as white powder; (mp 120-122° C.).

$R_f$=0.36 (cyclohexane/EtOAc, 1:1).

IR (neat, $v_{max}$/cm$^{-1}$) 3444 (O—H$_{bonded}$), 3056 (C—H, aromatic), 1727 (C=O, ester), 1650 (C=O, amide), 1624 (C=O, ketone), 1540 (C—C, aromatic), 1340 (C—O, ester), 1271 (C—N), 1238 (CH$_2$—N).

$^1$H NMR (300 MHz, CDCl$_3$) $\delta_H$ (ppm) 1.37 (t, J=7.1 Hz, 3H, CH$_3$), 4.37 (q, J=7.1 Hz, 2H, OCH$_2$), 5.23 (s, 2H, NCH$_2$), 6.84 (t, J=7.6 Hz, 1H), 7.05 (d, J=8.3 Hz, 1H), 7.36 (d, J=6.3 Hz, 1H), 7.37 (s, 5H), 7.49 (dd, J=11.4, 4.2 Hz, 1H), 8.14 (d, J=2.7 Hz, 1H, NCH$_{py}$), 8.50 (d, J=2.7 Hz 1H, CH$_{py}$), 11.35 (s, 1H, OH).

$^{13}$C NMR (75 MHz, CDCl$_3$) $\delta_C$ (ppm) 14.2 (CH$_3$), 53.2 (NCH$_2$), 61.5 (OCH$_2$), 115.7 (C$_q$), 118.4 (C$_q$), 118.7 (CH$_{aro}$), 119.0 (CH$_{aro}$), 120.2 (C$_q$), 128.7 (2×CH$_{aro}$), 128.8 (CH$_{aro}$), 129.2 (2×CH$_{aro}$), 131.3 (CH$_{aro}$), 134.7 (C$_q$), 136.4 (CH$_{aro}$), 143.5 (NCH$_{py}$), 146.2 (CH$_{py}$), 158.6 (C$_q$), 162.4 (C$_q$, amide), 164.0 (C$_q$, ester), 194.2 (C$_q$, ketone).

HRMS (ESI$^+$) calcd for C$_{22}$H$_{20}$NO$_5$ [M+H]$^+$ 378.1341, found 378.1336.

3-Ethoxycarbonyl-5-(o-hydroxybenzoyl)-1-(o-bromobenzyl)pyridin-2-one (CPADML7)

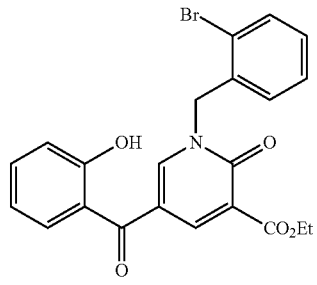 [SMILES: CCOC(=O)c1cc(C(=O)c2ccccc2O)cn(Cc2ccccc2Br)c1=O]

Synthesized according to (GP3A) by using a mixture of diester (1-3) (3.00 g, 9.5 mmol), and 2-bromobenzylamine (1.94 g, 10.44 mmol) in dichloromethane (10 mL) at room temperature and stirring for 3 hours. The final product precipitated and it was filtered and washed with cold diethyl ether (5 mL) to yield pyridone (CPADML7) (4.10 g, 87% yield) as yellow solid; (mp 172-174° C.).

$R_f$=0.24 (cyclohexane/EtOAc, 1:1).

IR (neat, $v_{max}$/cm$^{-1}$) 3448 (O—H$_{bonded}$), 3056 (C—H, aromatic), 1731 (C=O, ester), 1662 (C=O, amide), 1626 (C=O, ketone), 1544 (C—C, aromatic), 1342 (C—O, ester), 1281 (C—N), 1226 (CH$_2$—N), 1026 (C—Br).

$^1$H NMR (300 MHz, CDCl$_3$) $\delta_H$ (ppm) 1.38 (t, J=6.9 Hz, 3H, CH$_3$), 4.39 (q, J=6.8 Hz, 2H, OCH$_2$), 5.34 (s, 2H, NCH$_2$), 6.84-6.88 (m, 1H), 7.05 (d, J=8.3 Hz, 1H), 7.19-7.26 (m, 1H), 7.34 (t, J=6.9 Hz, 1H), 7.41-7.55 (m, 3H), 7.63 (d, J=7.8 Hz, 1H), 8.18 (s, 1H, NCH$_{py}$), 8.55 (s, 1H, CH$_{py}$), 11.34 (s, 1H, OH).

$^{13}$C NMR (75 MHz, CDCl$_3$) $\delta_C$ (ppm) 14.3 (CH$_3$), 53.3 (NCH$_2$), 61.7 (OCH$_2$), 115.8 (C$_q$), 118.4 (C$_q$), 118.8 (CH$_{aro}$), 119.0 (CH$_{aro}$), 120.6 (C$_q$), 124.2 (C$_q$), 128.4 (CH$_{aro}$), 130.6 (CH$_{aro}$), 131.5 (CH$_{aro}$), 132.1 (CH$_{aro}$), 133.4 (CH$_{aro}$), 133.6 (C$_q$), 136.5 (CH$_{aro}$), 143.7 (NCH$_{py}$), 146.2 (CH$_{py}$), 158.8 (C$_q$), 162.5 (C$_q$, amide), 164.0 (C$_q$, ester), 194.2 (C$_q$, ketone).

HRMS (ESI$^+$) calcd for C$_{22}$H$_{19}$BrNO$_5$ [M+H]$^+$ 456.0447, found 456.0440.

(Z)-2-[(Diethoxycarbonyl)methyl]-3-[(o-bromo)-benznylaminomethylene]chroman-4-one (1-9)

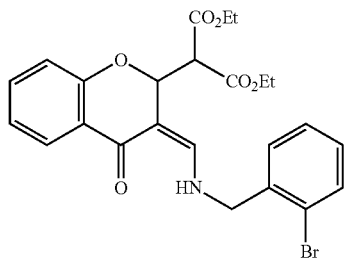 [SMILES: CCOC(=O)C(C(=O)OCC)C1Oc2ccccc2C(=O)/C1=C\NCc1ccccc1Br]

Synthesized according to (GP3A) by using a mixture of diester (1-3) (3.00 g, 9.5 mmol), and 2-bromobenzylamine (1.94 g, 10.44 mmol) in dichloromethane (10 mL) at room temperature and stirring for 3 hours. The enaminone (1-9) was obtained (0.23 g, 5% yield) after recrystallization from a mixture of methanol and diethyl ether (ratio 2:3, v/v) as transparent crystals; (mp 18-191° C.).

$R_f$=0.32 (cyclohexane/EtOAc, 4:1).

IR (neat, $v_{max}$/cm$^{-1}$) 1749 (C=O, ester), 1644 (C=O, ketone), 1466 (C—C, ester), 1138 (C—O, ester), 1025 (C—N), 755 (C—H, aromatic).

$^1$H NMR (300 MHz, CDCl$_3$) $\delta_H$ (ppm) 1.15 (t, J=7.1 Hz, 3H, CH$_3$), 1.27 (t, J=7.1 Hz, 3H, CH$_3$), 3.91 (d, J=10.4 Hz, 1H), 3.98-4.11 (m, 2H, OCH$_2$), 4.16-4.31 (m, 2H, OCH$_2$), 4.51 (d, J=6.3 Hz, 2H, NCH$_2$), 5.51 (d, J=10.4 Hz, 1H), 6.79-6.88 (m, 1H), 6.99-7.13 (m, 2H), 7.14-7.21 (m, 1H), 7.26-7.31 (m, 2H), 7.34-7.44 (m, 1H), 7.57 (d, J=7.5 Hz, 1H), 7.89 (dd, J=7.8, 1.7 Hz, 1H) 10.28-10.53 (m, 1H, NH).

$^{13}$C NMR (75 MHz, CDCl$_3$) $\delta_C$ (ppm) 14.0 (CH$_3$), 14.1 (CH$_3$), 53.2 (NCH$_2$), 57.1 (CH), 61.6 (OCH$_2$), 61.7 (OCH$_2$), 77.5 (CH), 98.1 (C$_q$), 118.0 (CH$_{aro}$), 121.9 (CH$_{aro}$), 123.0 (C$_q$), 126.2 (CH$_{aro}$), 127.9 (CH$_{aro}$), 129.2 (CH$_{aro}$), 129.6 (CH$_{aro}$), 133.1 (CH$_{aro}$), 134.1 (CH$_{aro}$), 136.6 (C$_q$), 153.1 (CH), 156.5 (C$_q$), 162.5 (C$_q$), 166.5 (C$_q$, ester), 166.6 (C$_q$, ester), 195.5 (C$_q$, ketone).

HRMS (ESI$^+$) calcd for C$_{24}$H$_{25}$BrNO$_6$ [M+1]$^+$ 502.0865, found 502.0799.

3-Ethoxycarbonyl-5-(o-hydroxybenzoyl)-1-(p-methoxybenzyl)pyridin-2-one (CPADML8)

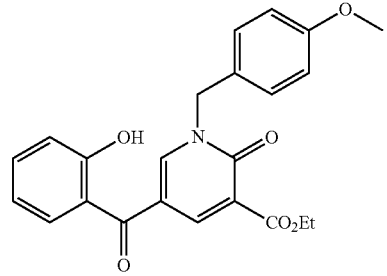 [SMILES: CCOC(=O)c1cc(C(=O)c2ccccc2O)cn(Cc2ccc(OC)cc2)c1=O]

Synthesized according to (GP3A) by using a mixture of diester (1-3) (0.50 g, 1.58 mmol) and p-methoxybenzylamine (0.24 g, 1.74 mmol) in dichloromethane (5 mL) and stirring during 3 hours at room temperature. Then the solvent was evaporated under reduced pressure and the crude product purified by silica gel column chromatography (70% cyclohexane in EtOAc) to lead pyridone (CPADML8) (0.57 g, 89% yield) as brownish oil.

$R_f$=0.45 (cyclohexane/EtOAc, 1:1).

IR (neat, $v_{max}$/cm$^{-1}$) 3220 (O—H$_{bonded}$), 3060 (C—H, aromatic), 2935 (C—H), 1731 (C=O, ester), 1654 (C=O, amide), 1602 (C=O, ketone), 1512 (C—C, aromatic), 1340 (C—O, ester), 1248 (C—O, aromatic), 1030 (C—O).

$^1$H NMR (300 MHz, CDCl$_3$): $\delta_H$ (ppm) 1.35 (t, J=7.1 Hz, 3H, CH$_3$), 3.77 (s, 1H, OCH$_3$), 4.34 (q, J=7.1 Hz, 2H, 2×OCH$_2$), 5.14 (s, 2H, NCH$_2$), 6.84 (dd, J=16.2, 7.9 Hz, 3H), 7.01 (d, J=8.2 Hz, 1H), 7.28-7.38 (m, 3H), 7.47 (7, J=7.0 Hz, 1H), 8.14 (s, 1H, NCH$_{py}$), 8.46 (s, 1H, CH$_{py}$), 11.31 (s, 1H, OH).

$^{13}$C NMR (75 MHz, CDCl$_3$) $\delta_C$ (ppm) 14.3 (CH$_3$), 52.8 (OCH$_3$), 53.3 (NCH$_2$), 61.5 (OCH$_2$), 114.6 (2×CH$_{aro}$), 115.7 (C$_q$), 118.6 (C$_q$), 118.8 (CH$_{aro}$), 119.0 (CH$_{aro}$), 120.2 (C$_q$), 126.8 (C$_q$), 130.4 (2×CH$_{aro}$), 131.4 (CH$_{aro}$), 136.4 (CH$_{aro}$), 143.5 (NCH$_{py}$), 146.3 (CH$_{py}$), 158.8 (C$_q$), 160.0 (C$_q$), 162.4 (C$_q$, amide), 164.1 (C$_q$, ester), 194.3 (C$_q$, ketone).

HRMS (ESI$^+$) calcd for C$_{23}$H$_{21}$NO$_6$Na [M+Na]$^+$ 430.1267, found 430.0804.

3-Ethoxycarbonyl-5-(o-hydroxybenzoyl)-1-(2,4,6-trimethylbenzyl)pyridin-2-one (CPADML9)

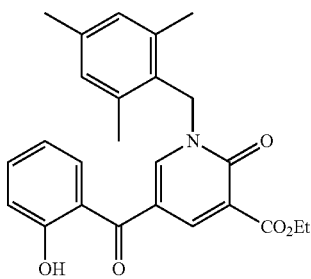 [SMILES: CCOC(=O)c1cc(C(=O)c2ccccc2O)cn(Cc2c(C)cc(C)cc2C)c1=O]

Synthesized according to (GP3A) by using a mixture of diester (1-3) (0.50 g, 1.58 mmol) and 2,4,6-trimethylbenzylamine (0.26 g, 1.74 mmol) in dichloromethane (5 mL) and stirring during 5 hours at room temperature. Then the solvent was evaporated under reduced pressure and the crude product purified by silica gel column chromatography (70% cyclohexane in EtOAc) to lead pyridone (CPADML9) (0.44 g, 67% yield) as orange oil.

$R_f$=0.32 (cyclohexane/EtOAc, 1:1).

IR (neat, $v_{max}$/cm$^{-1}$) 3390 (O—H$_{bonded}$), 2975 (C—H), 1731 (C=O, ester), 1650 (C=O, amide), 1646 (C=O, ketone), 1540 (C—C, aromatic), 1450 (CH$_3$), 1313 (C—O, ester), 1244 (CH$_2$—N), 764 (C—CH$_3$).

$^1$H NMR (300 MHz, CDCl$_3$) $\delta_H$ (ppm) 1.40 (t, J=7.1 Hz, 3H, CH$_3$), 2.20 (s, 6H, 2×CH$_3$), 2.28 (s, 3H, CH$_3$), 4.41 (q, J=7.1 Hz, 2H, OCH$_2$), 5.19 (s, 2H, NCH$_2$), 6.70 (t, J=7.5 Hz, 1H), 6.94 (s, 2H), 6.99 (d, J=8.3 Hz, 1H), 7.14 (d, J=7.8 Hz, 1H), 7.44 (t, J=7.8 Hz, 1H), 7.53 (d, J=2.3 Hz, 1H, NCH$_{py}$), 8.55 (d, J=2.3 Hz, 1H, CH$_{py}$), 11.35 (s, 1H, OH).

$^{13}$C NMR (75 MHz, CDCl$_3$) $\delta_C$ (ppm) 14.3 (CH$_3$), 19.6 (CH$_3$), 21.0 (CH$_3$), 30.9 (CH$_3$), 46.8 (NCH$_2$), 61.6 (OCH$_2$), 115.5 (C$_q$), 118.3 (C$_q$), 118.7 (CH$_{aro}$), 118.8 (CH$_{aro}$), 119.8 (C$_q$), 126.2 (C$_q$), 130.0 (2×CH$_{aro}$), 131.1 (CH$_{aro}$), 136.2 (CH$_{aro}$), 138.3 (C$_q$), 139.5 (C$_q$), 143.2 (NCH$_{py}$), 143.8 (CH$_{py}$), 159.3 (C$_q$), 162.4 (C$_q$, amide), 164.3 (C$_q$, ester), 194.2 (C$_q$, ketone), 206.9 (C$_q$).

HRMS (ESI$^+$) calcd for C$_{25}$H$_{26}$NO$_5$ [M+H]$^+$ 420.1811, found 420.1815.

3-Ethoxycarbonyl-5-(o-hydroxybenzoyl)-1-(phenethyl)pyridin-2-one (CPADML10)

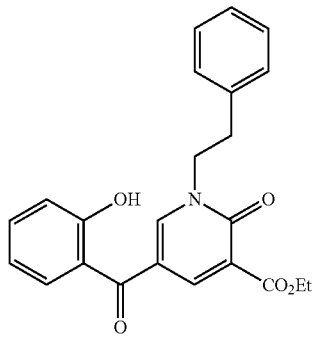 [SMILES: CCOC(=O)c1cc(C(=O)c2ccccc2O)cn(CCc2ccccc2)c1=O]

Synthesized according to (GP3A) by using a mixture of diester (1-3) (0.19 g, 0.60 mmol) and 2-phenethylamine (0.08 g, 0.66 mmol) in dichloromethane (5 mL) and stirring at room temperature during 3 hours at room temperature. The formed precipitate was then filtered and rinsed with cyclohexane to yield pure pyridone (CPADML10) (0.22 g, 92% yield) as pale yellow solid; (mp 158-160° C.).

$R_f$=0.19 (cyclohexane/EtOAc, 1:1).

IR (neat, $v_{max}$/cm$^{-1}$) 3444 (O—H$_{bonded}$), 3065 (C—H, aromatic), 1725 (C=O, ester), 1650 (C=O, amide), 1624 (C=O, ketone), 1536 (C—C, aromatic), 1344 (C—O, ester), 1269 (C—N), 1220 (CH$_2$—N).

$^1$H NMR (300 MHz, CDCl$_3$) $\delta_H$ (ppm) 1.40 (t, J=7.1 Hz, 3H, CH$_3$), 3.17 (t, J=6.0 Hz, 2H, CH$_2$), 4.24 (t, J=6.1 Hz, 2H, NCH$_2$), 4.40 (q, J=7.1 Hz, 2H, OCH$_2$), 6.72-6.77 (m, 2H), 7.01 (d, J=8.4 Hz, 1H), 7.14 (d, J=6.4 Hz, 2H), 7.28-7.38 (m, 3H), 7.46 (t, J=6.0 Hz, 1H), 7.56 (d, J=2.6 Hz, 1H, NCH$_{py}$), 8.54 (d, J=2.6 Hz, 1H, CH$_{py}$), 11.29 (s, 1H, OH).

$^{13}$C NMR (75 MHz, CDCl$_3$) $\delta_C$ (ppm) 14.2 (CH$_3$), 34.2 (CH$_2$), 54.1 (NCH$_2$), 61.6 (OCH$_2$), 114.9 (C$_q$), 118.3 (C$_q$), 118.6 (CH$_{aro}$), 119.1 (CH$_{aro}$), 120.3 (C$_q$), 127.1 (CH$_{aro}$), 129.0 (2×CH$_{aro}$), 129.1 (2×CH$_{aro}$), 131.0 (CH$_{aro}$), 136.1 (CH$_{aro}$), 137.2 (C$_q$), 144.0 (NCH$_{py}$), 147.0 (CH$_{py}$), 158.6 (C$_q$), 162.3 (C$_q$, amide), 164.1 (C$_q$, ester), 194.0 (C$_q$, ketone).

HRMS (ESI$^+$) calcd for C$_{23}$H$_{22}$NO$_5$ [M+H]$^+$ 392.1497, found 392.1492.

3-Ethoxycarbonyl-5-(o-hydroxybenzoyl)-1-(p-chlorophenethyl)pyridin-2-one (CPADML11)

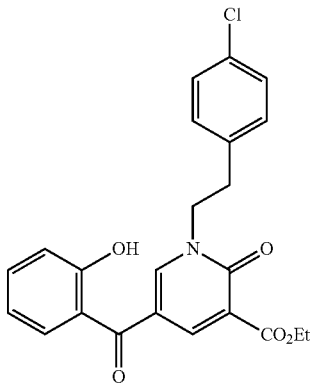 [SMILES: CCOC(=O)c1cc(C(=O)c2ccccc2O)cn(CCc2ccc(Cl)cc2)c1=O]

Synthesized according to (GP3A) by using a mixture of diester (1-3) (0.50 g, 1.58 mmol) and 2-phenethylamine (0.271 g, 1.74 mmol) in dichloromethane (5 mL) and stirring at room temperature during 5 hours at room temperature. Diethyl ether was added and the formed precipitate was then filtered and rinsed with cyclohexane to yield pyridone (CPADML11) (0.42 g, 62% yield) as white solid (mp 138-140° C.).

$R_f$=0.19 (cyclohexane/EtOAc, 1:1).

IR (neat, $v_{max}$/cm$^{-1}$) 3448 (O—H$_{bonded}$), 3060 (C—H, aromatic), 2935 (C—H), 1727 (C=O, ester), 1650 (C=O, amide), 1598 (C=O, ketone), 1536 (C—C, aromatic), 1342 (C—O, ester), 1267 (C—O, aromatic), 762 (C—Cl).

$^1$H NMR (300 MHz, CDCl$_3$) $\delta_H$ (ppm) 1.40 (t, J=7.1 Hz, 3H, CH$_3$), 3.15 (t, J=6.3 Hz, 2H, CH$_2$), 4.22 (t, J=6.4 Hz, 2H, NCH$_2$), 4.40 (q, J=7.1 Hz, 2H, OCH$_2$), 6.80-6.90 (m, 2H), 7.04 (d, J=8.4 Hz, 1H), 7.10 (d, J=8.1 Hz, 2H), 7.33 (d, J=8.0 Hz, 2H), 7.49 (t, J=6.9 Hz, 1H), 7.62 (d, J=2.5 Hz, 1H, NCH$_{py}$), 8.55 (d, J=2.5 Hz, 1H, CH$_{py}$), 11.28 (s, 1H, OH).

$^{13}$C NMR (75 MHz, CDCl$_3$) $\delta_C$ (ppm) 14.3 (CH$_3$), 33.7 (CH$_2$), 53.9 (NCH$_2$), 61.7 (OCH$_2$), 115.3 (C$_q$), 118.3 (C$_q$), 118.8 (CH$_{aro}$), 119.2 (CH$_{aro}$), 120.6 (C$_q$), 129.2 (2×CH$_{aro}$), 130.5 (2×CH$_{aro}$), 130.9 (CH$_{aro}$), 133.2 (C$_q$), 135.7 (C$_q$), 136.1 (CH$_{aro}$), 144.0 (NCH$_{py}$), 146.6 (CH$_{py}$), 158.6 (C$_q$), 162.4 (C$_q$, amide), 164.0 (C$_q$, ester), 194.0 (C$_q$, ketone).

HRMS (ESI$^+$) calcd for C$_{23}$H$_{20}$ClNO$_5$Na [M+Na]$^+$ 448.0928, found 448.0912.

3-Ethoxycarbonyl-5-(o-hydroxybenzoyl)-1-(indol-3-yl-ethyl)pyridin-2-one (CPADML12)

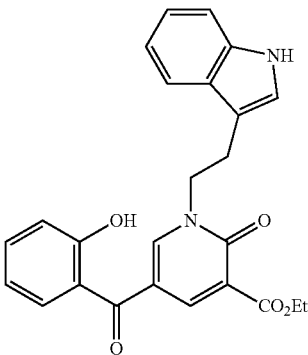 [SMILES: CCOC(=O)c1cc(C(=O)c2ccccc2O)cn(CCc2c[nH]c3ccccc23)c1=O]

Synthesized according to (GP3B) by using a previously stirred mixture of diester (1-3) (0.50 g, 1.58 mmol), CsF (12 mg, 0.08 mmol) and tryptamine (0.27 g, 1.74 mmol) in dichloromethane (5 mL) at room temperature and stirring for 1 hour. Diethyl ether (3 mL) was then added and the formed precipitate filtered and rinsed with cyclohexane to yield pyridone (CPADML12) (0.63 g, 93% yield) as yellow solid; (mp 237-239° C.).

$R_f$=0.21 (cyclohexane/EtOAc, 1:1).

IR (neat, $v_{max}$/cm$^{-1}$) 3314 (N—H), 3056 (C—H, aromatic), 1729 (C=O, ester), 1660 (C=O, amide), 1626 (C=O, ketone), 1592 (C—C, aromatic), 1340 (C—O, ester), 1271 (C—N), 1224 (CH$_2$—N), 1174 (C—N).

$^1$H NMR (300 MHz, CDCl$_3$) $\delta_H$ (ppm) 1.41 (t, J=7.1 Hz, 3H, CH$_3$), 3.34 (t, J=6.3 Hz, 2H, CH$_2$), 4.31 (t, J=6.3 Hz, 2H, NCH$_2$), 4.42 (q, J=7.1 Hz, 2H, OCH$_2$), 6.52 (d, J=4.2 Hz, 2H), 6.92-7.01 (m, 2H), 7.10 (t, J=7.4 Hz, 1H), 7.21 (t, J=7.5 Hz, 1H), 7.37-7.43 (m, 2H), 7.49-7.52 (m, 2H, H$_{am}$, NCH$_{py}$), 8.30 (s, 1H, NH), 8.52 (d, J=2.4 Hz, 1H, CH$_{py}$), 11.22 (s, 1H, OH).

$^{13}$C NMR (75 MHz, CDCl$_3$) $\delta_C$ (ppm) 14.3 (CH$_3$), 24.1 (CH$_2$), 53.1 (NCH$_2$), 61.6 (OCH$_2$), 111.2 (C$_q$), 111.5 (CH$_{aro}$), 114.9 (C$_q$), 118.2 (CH$_{aro}$), 118.3 (C$_q$), 118.5 (CH$_{aro}$), 119.0 (CH$_{aro}$), 120.1 (CH$_{aro}$), 120.2 (C$_q$), 122.6 (CH$_{aro}$), 123.1 (CH$_{aro}$), 127.0 (C$_q$), 130.9 (CH$_{aro}$), 136.1 (CH$_{aro}$), 136.4 (C$_q$), 143.9 (NCH$_{py}$), 147.2 (CH$_{py}$), 158.8 (C$_q$), 162.2 (C$_q$, amide), 164.2 (C$_q$, ester), 194.9 (C$_q$, ketone).

HRMS (ESI$^+$) calcd for C$_{25}$H$_{23}$N$_2$O$_5$ [M+H]$^+$ 431.1618, found 431.1607.

(Z)-2-[(Diethoxycarbonyl)methyl]-3-[indol-3-yl-ethyl)aminomethylene]chroman-4-one (1-10)

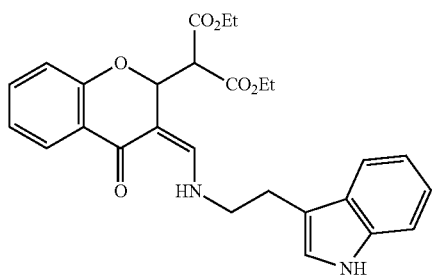 [SMILES: CCOC(=O)C(C(=O)OCC)C1Oc2ccccc2C(=O)/C1=C\NCCc1c[nH]c2ccccc12]

Synthesized according to (GP3A) by using a mixture of diester (1-3) (0.10 g, 0.32 mmol), and tryptamine (0.05 g, 0.35 mmol) in dichloromethane (3 mL) at room temperature and stirring for 1 hour. Purification by silica gel column chromathography (80% cyclohexane in EtOAc) yielded enaminochromanone (1-10) (0.07 g, 44% yield) as orange oil.

$R_f$=0.19 (cyclohexane/EtOAc, 4:1).

IR (neat, $v_{max}$/cm$^{-1}$) 3315 (N—H), 2981 (C—H, aromatic), 1726 (C=O, ester), 1644 (C=O, ketone), 1606 (C—C, aromatic), 1464 (C—C, ester), 1145 (C—O, ester), 1026 (C—N).

$^1$H NMR (300 MHz, CDCl$_3$) $\delta_H$ (ppm) 1.13 (t, J=7.1 Hz, 3H, CH$_3$), 1.27 (t, J=7.1 Hz, 3H, CH$_3$), 3.03 (t, J=6.8 Hz, 2H, CH$_2$), 3.44-3.70 (m, 2H, CH$_2$), 3.89 (d, J=10.3 Hz, 1H, CH), 4.02 (q, J=7.1 Hz, 2H, OCH$_2$), 4.17-4.29 (m, 2H, OCH$_2$), 5.43 (d, J=10.3 Hz, 1H, OCH), 6.83 (d, J=8.2 Hz, 1H), 6.93 (d, J=13.0 Hz, 1H, CH), 6.96-7.06 (m, 2H), 7.11 (d, J=7.4 Hz, 1H), 7.19 (t, J=7.4 Hz, 1H), 7.32 (d, J=7.7 Hz, 1H), 7.38 (t, J=7.4 Hz, 1H), 7.55 (d, J=7.8 Hz, 1H), 7.89 (d, J=7.5 Hz, 1H), 8.26 (bs, 1H, NH$_{indole}$), 10.06-10.30 (m, 1H, NH).

$^{13}$C NMR (75 MHz, CDCl$_3$) $\delta_C$ (ppm) 13.8 (CH$_3$), 14.0 (CH$_3$), 27.0 (CH$_2$), 49.6 (NHCH$_2$), 57.1 (CH), 61.4 (OCH$_2$), 61.6 (OCH$_2$), 77.5 (CH), 97.0 (C$_q$), 111.3 (C$_q$), 111.4 (CH$_{aro}$), 117.8 (CH$_{aro}$), 118.1 (CH$_{aro}$), 119.3 (CH$_{aro}$), 121.8 (CH$_{aro}$), 122.0 (CH$_{aro}$), 122.5 (CH), 123.0 (C$_q$), 126.0 (CH$_{aro}$), 126.8 (C$_q$), 133.8 (CH$_{aro}$), 136.3 (C$_q$), 153.2 (CH), 156.2 (C$_q$), 166.4 (C$_q$, ester), 166.6 (C$_q$, ester), 179.9 (C$_q$, ketone).

HRMS (ESI$^+$) calcd for C$_{27}$H$_{29}$N$_2$O$_6$ [M+H]$^+$ 477.2025, found 477.2027.

3-Ethoxycarbonyl-5-(o-hydroxybenzoyl)-1-(pentyl)pyridin-2-one (CPADML14)

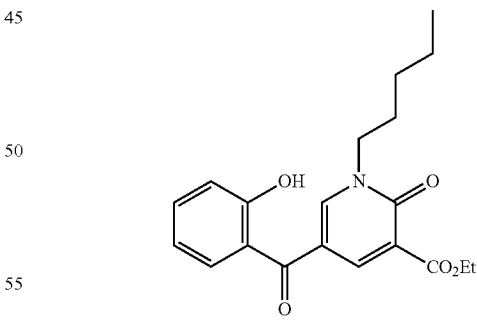

Synthesized according to (GP3A) by using a mixture of diester (1-3) (2.00 g, 6.32 mmol) and n-pentylamine (0.61 g, 6.96 mmol) in dichloromethane (10 mL) and stirring during 3 hours at room temperature. Then the solvent was evaporated under reduced pressure and the crude product purified by silica gel column chromatography (50% cyclohexane in EtOAc) to yield pyridone (CPADML14) (2.12 g, 94% yield) as yellow oil.

$R_f$=0.41 (cyclohexane/EtOAc, 1:1).

IR (neat, $v_{max}$/cm$^{-1}$) 3006 (C—H, aromatic), 1725 (C=O, ester), 1593 (C—C, aromatic), 1648 (C=O, amide), 1619 (C=O, ketone), 1593 (C—C, aromatic), 1531 (CH$_2$—CH$_3$), 1338 (C—O, ester), 1275 (C—N), 1261 (CH$_2$—N).

$^1$H NMR (300 MHz, CDCl$_3$) $\delta_H$ (ppm) 0.91 (t, J=6.6 Hz, 3H, CH$_{3\ pentyl}$), 1.30-1.42 (m, 4H, 2×CH$_2$), 1.38 (t, J=7.0 Hz, 3H, CH$_3$), 1.76-1.87 (m, 2H, CH$_2$), 4.00-4.10 (m, 2H, NCH$_2$), 4.38 (q, J=7.1 Hz, 2H, OCH$_2$), 6.95 (t, J=7.6 Hz, 1H), 7.09 (d, J=8.8 Hz, 1H), 7.50-7.60 (m, 2H), 8.14 (d, J=2.6 Hz, 1H, NCH$_{py}$), 8.51 (d, J=2.6 Hz, 1H, CH$_{py}$), 11.38 (s, 1H, OH).

$^{13}$C NMR (75 MHz, CDCl$_3$) $\delta_C$ (ppm) 13.9 (CH$_{3\ pentyl}$), 14.2 (CH$_3$), 22.2 (CH$_2$), 28.7 (CH$_2$), 28.8 (CH$_2$), 51.6 (NCH$_2$), 61.6 (OCH$_2$), 115.6 (C$_q$), 118.6 (C$_q$), 118.9 (CH$_{aro}$), 119.1 (CH$_{aro}$), 120.0 (C$_q$), 131.4 (CH$_{aro}$), 136.5 (CH$_{aro}$), 143.6 (NCH$_{py}$), 146.5 (CH$_{py}$), 158.6 (C$_q$), 162.2 (C$_q$, amide), 164.3 (C$_q$, ester), 194.5 (C$_q$, ketone).

HRMS (ESI$^+$) calcd for C$_{20}$H$_{23}$NO$_5$Na [M+Na]$^+$ 380.1474, found 380.1463.

3-Ethoxycarbonyl-5-[(5-benzyloxy)-o-hydroxybenzoyl]-pyridin-2-one (CPADML17)

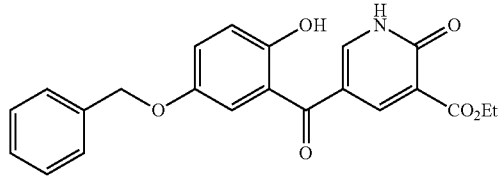 [SMILES: CCOC(=O)c1cc(C(=O)c2cc(OCc3ccccc3)ccc2O)c[nH]c1=O]

Synthesized according to (GP3A) by using a mixture of diester (1-8) (0.42 g, 1.00 mmol), and a solution of ammonium hydroxide (33% ammonia in water) (0.10 g, 2.00 mmol) in ethanol (10 mL) at room temperature and stirring for 1 hour. The product precipitated and the solid obtained was filtered and washed with diethyl ether (5 mL) to isolate the pyridone (CPADML17) (0.35 g, 89% yield) as orange solid; (mp 166-168° C.).

$R_f$=0.28 (cyclohexane/EtOAc, 1:4).

IR (neat, $v_{max}$/cm$^{-1}$) 1724 (C=O, ester), 1650 (C=O, amide), 1626 (C=O, ketone), 1561 (C—C, aromatic), 1432 (C—C, aromatic), 1233 (C—O, ester), 1200 (C—O).

$^1$H NMR (300 MHz, CDCl$_3$) $\delta_H$ (ppm) 1.31 (t, J=7.1 Hz, 3H, CH$_3$), 4.29 (q, J=7.1 Hz, 2H, OCH$_2$), 4.96 (s, 2H, OCH$_2$), 7.00 (d, J=9.1 Hz, 1H), 7.06 (d, J=2.3 Hz, 1H), 7.20 (d, J=9.0 Hz, 1H), 7.28-7.38 (m, 5H), 8.34 (s, 1H, NCH$_{py}$), 8.62 (d, J=1.9 Hz, 1H, CH$_{py}$), protons from NH and OH groups were not observed.

$^{13}$C NMR (75 MHz, CDCl$_3$) $\delta_C$ (ppm) 14.2 (CH$_3$), 61.6 (OCH$_2$), 71.1 (OCH$_2$), 116.1 (CH$_{aro}$), 118.5 (C$_q$), 119.7 (CH$_{aro}$), 123.9 (C$_q$), 125.0 (CH$_{aro}$), 127.4 (2×CH$_{aro}$), 128.2 (CH$_{aro}$), 128.7 (2×CH$_{aro}$), 132.2 (C$_q$), 136.5 (C$_q$), 144.9 (NCH$_{py}$), 146.0 (CH$_{py}$), 150.9 (C$_q$), 156.8 (C$_q$), 162.9 (C$_q$, amide), 164.3 (C$_q$, ester), 194.2 (C$_q$, ketone).

HRMS (ESI$^+$) calcd for C$_{22}$H$_{19}$NO$_6$Na [M+Na]$^+$ 416.1110, found 416.1102.

3-Ethoxycarbonyl-5-[(5-benzyloxy)-o-hydroxybenzoyl]-1-(pentyl)pyridin-2-one (CPADML18)

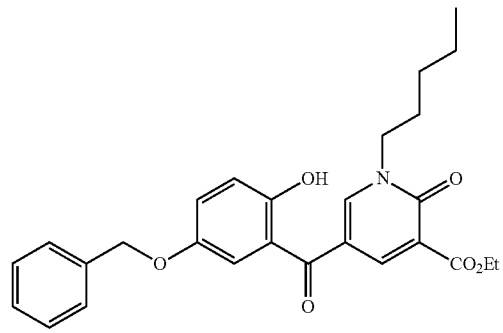 [SMILES: CCCCCn1cc(C(=O)c2cc(OCc3ccccc3)ccc2O)cc(C(=O)OCC)c1=O]

Synthesized according to (GP3A) by using a mixture of diester (1-8) (0.20 g, 0.47 mmol) and n-pentylamine (0.06 g, 0.71 mmol) in dichloromethane (3 mL) and stirring during 3 hours. Then the solvent was evaporated under reduced pressure and the crude product purified by silica gel column chromatography (50% cyclohexane in EtOAc) to yield the pyridone (CPADML18) (0.37 g, 79% yield) as yellow solid; (mp 151-153° C.).

$R_f$=0.32 (cyclohexane/EtOAc, 3:1).

IR (neat, $v_{max}$/cm$^{-1}$) 2926 (C—H), 1720 (C=O, ester), 1648 (C=O, amide), 1535 (C—C, aromatic), 1269 (C—O, ester), 1211 (CH$_2$—N), 736 (C—H, aromatic).

$^1$H NMR (300 MHz, CDCl$_3$) $\delta_H$ (ppm) 0.89 (t, J=6.6 Hz, 3H, CH$_{3\ pentyl}$), 1.30-1.40 (m, 4H, 2×CH$_2$), 1.37 (t, J=7.1 Hz, 3H, CH$_3$), 1.74-1.87 (m, 2H, CH$_2$), 3.94-4.04 (m, 2H, NCH$_2$), 4.38 (q, J=7.1 Hz, 2H, OCH$_2$), 5.01 (s, 2H, OCH$_2$), 7.00-7.08 (m, 2H), 7.17-7.25 (m, 1H), 7.30-7.45 (m, 5H), 8.10 (d, J=2.6 Hz, 1H, CH$_{py}$), 8.53 (d, J=2.6 Hz, 1H, NCH$_{py}$), 10.93 (s, 1H, OH).

$^{13}$C NMR (75 MHz, CDCl$_3$) $\delta_C$ (ppm) 13.8 (CH$_{3\ pentyl}$), 14.3 (CH$_3$), 22.2 (CH$_2$), 28.7 (CH$_2$), 28.9 (CH$_2$), 51.6 (NCH$_2$), 61.6 (OCH$_2$), 71.0 (OCH$_2$), 115.5 (C$_q$), 115.6 (CH$_{aro}$), 118.2 (C$_q$), 119.8 (CH$_{aro}$), 120.0 (C$_q$), 125.1 (CH$_{aro}$), 127.3 (2×CH$_{aro}$), 128.2 (CH$_{aro}$), 128.7 (2×CH$_{aro}$), 136.4 (C$_q$), 143.3 (NCH$_{py}$), 146.4 (CH$_{py}$), 150.9 (C$_q$), 156.9 (C$_q$), 158.6 (C$_q$, amide), 164.2 (C$_q$, ester), 194.0 (C$_q$, ketone).

HRMS (ESI$^+$) calcd for C$_{27}$H$_{30}$NO$_6$ [M+H]$^+$ 464.2073, found 464.2067.

3-Ethoxycarbonyl-5-(o-hydroxybenzoyl)-pyridin-2-one (1-11)

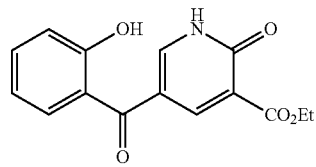 [SMILES: CCOC(=O)c1cc(C(=O)c2ccccc2O)c[nH]c1=O]

Synthesized according to (GP3A) by using a mixture of diester (1-3) (1.00 g, 3.16 mmol), and a solution of ammonium hydroxide (33% ammonia in water) (0.33 g, 6.32 mmol) in ethanol (10 mL) at room temperature and stirring for 1 hour. The product precipitated and the solid obtained was filtered to obtain pyridone (1-11) (0.87 g, 96% yield) as white solid; (mp 120-122° C., 139° C.).

$R_f$=0.12 (cyclohexane/EtOAc, 1:1).

IR (neat, $v_{max}$/cm$^{-1}$) 1732 (C=O, ester), 1680 (C=O, amide), 1622 (C=O, ketone), 1583 (C—C, aromatic), 1338 (C—O, ester), 1223 (C—N).

$^1$H NMR (300 MHz, MeOD) $\delta_H$ (ppm) 1.36 (t, J=7.1 Hz, 3H, CH$_3$), 4.33 (q, J=7.1 Hz, 2H, OCH$_2$), 6.72-7.14 (m, 2H), 7.49 (dd, J=15.1, 7.5 Hz, 1H), 8.17 (s, 1H, NCH$_{py}$), 8.62 (s, 1H, CH$_{py}$), protons from NH and OH groups were not observed.

$^{13}$C NMR (75 MHz, CDCl$_3$) $\delta_C$ (ppm) 14.2 (CH$_3$), 61.7 (OCH$_2$), 118.2 (C$_q$), 118. (CH$_{aro}$), 118.8 (CH$_{aro}$), 119.3 (CH$_{aro}$), 121.1 (C$_q$), 131.7 (NCH$_{py}$), 136.6 (CH$_{aro}$), 145.3 (CH$_{py}$), 156.6 (C$_q$), 162.4 (C$_q$, amide), 162.6 (C$_q$), 163.8 (C$_q$, ester), 194.5 (C$_q$, ketone).

HRMS (ESI$^+$) calcd for C$_{15}$H$_{13}$NO$_5$Na [M+Na]$^+$ 310.2566, found 310.2561.

Physical and H NMR spectral data are in accordance with those previously reported.

3-Ethoxycarbonyl-5-(o-methoxybenzoyl)-1-(pentyl)pyridin-2-one (CPADML15)

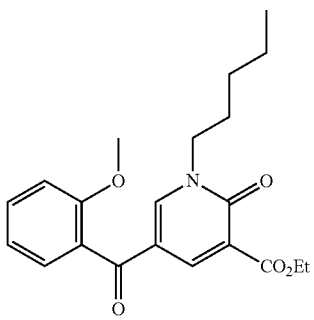 [SMILES: CCCCCn1cc(C(=O)c2ccccc2OC)cc(C(=O)OCC)c1=O]

Synthesized according to (GP4) by using a previously heated mixture of pyridone (CPADML14) (0.30 g, 0.84 mmol), K$_2$CO$_3$ (0.29 g, 2.10 mmol), KI (14 mg, 0.08 mmol) and 18-C-6 (2 mg, 0.008 mmol) in toluene (5 mL). The iodomethane (0.24 g, 1.68 mmol) was then added and the reaction was stirred at 40° C. for 2 hours then kept at room temperature overnight. Filtration through celite and evaporation of solvent afforded an orange yellow which was purified by column chromatography (80% cyclohexane in EtOAc) to yield as final product the pyridone (CPADML15) (0.29 g, 94% yield) as white-off solid; (mp 147-149° C.).

$R_f$=0.40 (cyclohexane/EtOAc, 4:1).

IR (neat, $v_{max}$/cm$^{-1}$) 3063 (C—H, aromatic), 2932 (C—H, aliphatic), 1737 (C=O, ester), 1648 (C=O, amide), 1627 (C=O, ketone), 1599 (C—C, aromatic), 1317 (C—O, ester), 1255 (C—O, aromatic), 1130 (C—O).

$^1$H NMR (300 MHz, CDCl$_3$) $\delta_H$ (ppm) 0.88 (t, J=6.7 Hz, 3H, CH$_{3\ pentyl}$), 1.26-1.34 (m, 4H, 2×CH$_2$), 1.34 (t, J=7.1 Hz, 3H, CH$_3$), 1.69-1.85 (m, 2H, CH$_2$), 3.76 (s, 3H, OCH$_3$), 3.91-4.04 (m, 2H, NCH$_2$), 4.33 (q, J=7.1 Hz, 2H, OCH$_2$), 6.99 (d, J=8.4 Hz, 1H), 7.06 (t, J=7.5 Hz, 1H), 7.37 (d, J=7.5 Hz, 1H), 7.49 (t, J=7.9 Hz, 1H), 8.13 (d, J=2.6 Hz, 1H, NCH$_{py}$), 8.44 (d, J=2.6 Hz, 1H, CH$_{py}$).

$^{13}$C NMR (75 MHz, CDCl$_3$) $\delta_C$ (ppm) 13.8 (CH$_{3\ pentyl}$), 14.2 (CH$_3$), 22.1 (CH$_2$), 28.5 (CH$_2$), 28.7 (CH$_2$), 51.3 (NCH$_2$), 55.5 (OCH$_3$) 61.3 (OCH$_2$), 111.4 (CH$_{aro}$), 116.5 (C$_q$), 119.4 (C$_q$), 121.1 (CH$_{aro}$), 127.0 (C$_q$), 129.7 (CH$_{aro}$), 132.7 (CH$_{aro}$), 143.8 (NCH$_{py}$), 147.1 (CH$_{py}$), 156.7 (C$_q$), 158.9 (C$_q$, amide), 164.5 (C$_q$, ester), 190.7 (C$_q$, ketone).

HRMS (ESI$^+$) calcd for C$_{21}$H$_{26}$NO$_5$ [M+H]$^+$ 372.1811, found 372.1811.

3-Ethoxycarbonyl-5-(o-pentyloxybenzoyl)-1-(benzyl)pyridin-2-one (CPADML16)

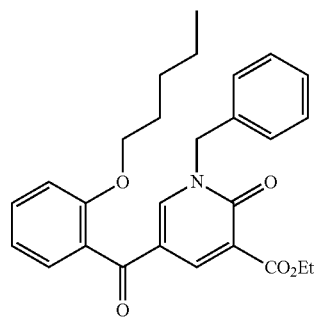 [SMILES: CCCCCOc1ccccc1C(=O)c1cc(C(=O)OCC)c(=O)n(Cc2ccccc2)c1]

Synthesized according to (GP4) by using a previously heated mixture of pyridone (CPADML6) (0.26 g, 0.69 mmol), K$_2$CO$_3$ (0.24 g, 1.72 mmol), KI (12 mg, 0.07 mmol) and 18-C-6 (2 mg, 0.007 mmol) in toluene (5 mL). The n-bromopentane (0.21 g, 1.38 mmol) was then added and the reaction was stirred at 115° C. for 2 hours then kept at room temperature for additionally 16 hours. Filtration through celite and evaporation of solvent led brown oil which was purified by column chromatography (70% cyclohexane in EtOAc) to yield pyridone (CPADML16) (0.30 g, 98% yield) as yellow oil.

$R_f$=0.42 (cyclohexane/EtOAc, 3:1).

IR (neat, $v_{max}$/cm$^{-1}$) 2951 (C—H), 1729 (C=O, ester), 1637 (C=O, amide), 1446 (C—C, aromatic), 1220 (C—N), 1213 (CH$_2$—N), 703 (C—H, aromatic).

$^1$H NMR (300 MHz, CDCl$_3$) $\delta_H$ (ppm) 0.75 (t, J=7.0 Hz, 3H, CH$_{3\ pentyl}$), 1.04-1.21 (m, 4H, 2×CH$_2$), 1.33 (t, J=7.1 Hz, 3H, CH$_3$), 1.37-1.45 (m, 2H, CH$_2$), 3.79 (t, J=6.5 Hz, 2H, OCH$_2$), 4.33 (q, J=7.1 Hz, 2H, OCH$_2$), 5.15 (s, 2H, NCH$_2$), 6.89 (d, J=8.4 Hz, 1H), 7.00 (t, J=7.4 Hz, 1H), 7.30 (s, 5H), 7.34 (d, J=7.6 Hz, 1H), 7.43 (t, J=7.8 Hz, 1H), 8.14 (d, J=2.3 Hz, 1H, NCH$_{py}$), 8.46 (d, J=2.3 Hz, 1H, CH$_{py}$).

$^{13}$C NMR (75 MHz, CDCl$_3$) $\delta_C$ (ppm) 13.7 (CH$_{3\ pentyl}$), 14.1 (CH$_3$), 22.0 (CH$_2$), 27.7 (CH$_2$), 28.3 (CH$_2$), 53.1 (NCH$_2$), 61.2 (OCH$_2$), 68.3 (OCH$_2$), 112.0 (CH$_{aro}$), 117.0 (C$_q$), 119.6 (C$_q$), 120.9 (CH$_{aro}$), 127.0 (C$_q$), 128.4 (3×CH$_{aro}$), 128.9 (2×CH$_{aro}$), 129.8 (CH$_{aro}$), 132.7 (CH$_{aro}$), 134.9 (C$_q$), 143.8 (NCH$_{py}$), 146.6 (CH$_{py}$), 156.2 (C$_q$), 158.9 (C$_q$, amide), 164.2 (C$_q$, ester), 190.7 (C$_q$, ketone).

HRMS (ESI$^+$) calcd for C$_{27}$H$_{30}$NO$_5$ [M+H]$^+$ 448.2124, found 448.2120.

5-(o-Hydroxybenzoyl)-pyridin-2-one-3-carboxylic acid (CPADML19)

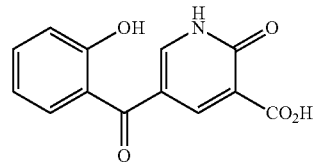 [SMILES: O=C(c1c[nH]c(=O)c(C(=O)O)c1)c1ccccc1O]

Synthesized according (GP5) by using the pyridone ester (1-11) (0.49 g, 1.71 mmol) in HCl/Ac$_2$O (4 mL) and stirring for 2 hours at 90° C. After precipitation the product was filtered and washed to yield pyridone acid (CPADML19) (0.40 g, 90% yield) as yellow solid; (mp 236-238° C.).

R$_f$=0.15 (cyclohexane/EtOAc, 1:1).

IR (neat, v$_{max}$/cm$^{-1}$) 3065 (C—H, aromatic), 2904 (C=O, acid), 1706 (C=O, amide), 1626 (C=O, ketone), 1587 (C—C, aromatic), 1348 (C—O, ester), 12170 (C—N).

$^1$H NMR (300 MHz, DMSO-d$_6$) δ$_H$ (ppm) 6.91-7.08 (m, 2H), 7.39 (d, J=7.5 Hz, 1H), 7.45 (t, J=7.8 Hz, 1H), 8.22 (d, J=2.5 Hz, 1H, NCH$_{py}$), 8.54 (d, J=2.4 Hz, 1H, CH$_{py}$), 10.33 (bs, 1H, NH), 13.6 (bs, 1H, OH$_{carboxylic\ acid}$).

$^{13}$C NMR (75 MHz, DMSO-d$_6$) δ$_C$ (ppm) 105.9 (C$_q$), 117.9 (CH$_{aro}$), 119.4 (CH$_{aro}$), 122.7 (C$_q$), 124.4 (C$_q$), 129.7 (CH$_{aro}$), 135.3 (CH$_{aro}$), 142.4 (CH$_{py}$), 144.6 (NCH$_{py}$), 161.9 (C$_q$), 164.2 (C$_q$, amide), 165.9 (C$_q$, acid), 191.6 (C$_q$, ketone).

HRMS (ESI$^-$) calcd for C$_{13}$H$_8$NO$_5$ [M−H]$^+$ 258.0402, found 258.0486.

5-(o-Hydroxybenzoyl)-1-(benzyl)pyridin-2-one-3-carboxylic acid (CPADML20)

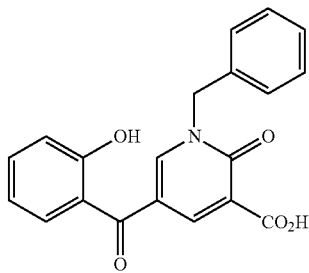 [SMILES: O=C(c1cc(C(=O)O)c(=O)n(Cc2ccccc2)c1)c1ccccc1O]

Synthesized according to (GP5) by using pyridone ester (CPADML6) (0.87 g, 2.30 mmol) in HCl/Ac$_2$O (6 mL) and stirring for 2 hours at 90° C. After precipitation the product was filtered and washed to yield pyridone acid (CPADML20) (0.75 g, 77% yield) as white solid; (mp 201-203° C.).

R$_f$=0.35 (DCM/EtOAc, 3:1).

IR (neat, v$_{max}$/cm$^{-1}$) 3232 (O—H$_{bonded}$), 1711 (C=O, amide), 1439 (C—C, aromatic), 1299 (C—O, acid), 749 (C—H, aromatic).

$^1$H NMR (300 MHz, CDCl$_3$) δ$_H$ (ppm) 5.34 (s, 2H, NCH$_2$), 6.90 (t, J=7.6 Hz, 1H), 7.08 (d, J=8.3 Hz, 1H), 7.34-7.46 (m, 6H), 7.30 (s, 5H), 7.34 (d, J=7.6 Hz, 1H), 7.54 (t, J=7.9 Hz, 1H), 8.23 (d, J=2.4 Hz, 1H, NCH$_{py}$), 8.86 (d, J=2.4 Hz, 1H, CH$_{py}$), 11.31 (s, 1H, OH), 13.72 (bs, 1H, OH$_{carboxylic\ acid}$).

$^{13}$C NMR (75 MHz, CDCl$_3$) δ$_C$ (ppm) 54.0 (NCH$_2$), 102.0 (C$_q$), 117.4 (C$_q$), 118.1 (C$_q$), 119.1 (CH$_{aro}$), 119.3 (C$_q$), 119.4 (CH$_{aro}$), 128.8 (2×CH$_{aro}$), 129.5 (CH$_{aro}$), 129.6 (2×CH$_{aro}$), 131.5 (CH$_{aro}$), 133.5 (C$_q$), 137.2 (CH$_{aro}$), 145.2 (NCH$_{py}$), 145.6 (CH$_{py}$), 162.9 (C$_q$, amide), 164.0 (C$_q$, acid), 193.8 (C$_q$, ketone).

HRMS (ESI$^+$) calcd for C$_{15}$H$_{16}$NO$_5$ [M+H]$^+$ 350.1028, found 350.1034.

5-(o-Hydroxybenzoyl)-1-(pentyl)pyridin-2-one-3-carboxylic acid (CPADML21)

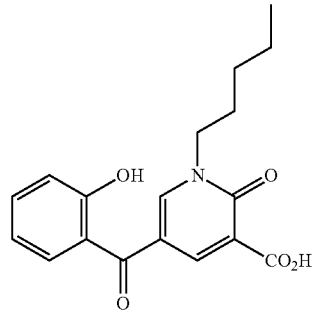 [SMILES: CCCCCn1cc(C(=O)c2ccccc2O)cc(C(=O)O)c1=O]

Synthesized according to (GP5) by using the pyridone ester (CPADML14) (0.15 g, 0.42 mmol) in HCl/Ac$_2$O (4 mL) and stirring for 2 hours at 90° C. After precipitation the product was filtered and washed to yield pyridone acid (CPADML21) (0.11 g, 83% yield) as pale yellow solid; (mp 164-166° C.).

R$_f$=0.25 (cyclohexane/EtOAc, 1:3).

IR (neat, v$_{max}$/cm$^{-1}$) 2957 (C—H), 1725 (C=O, acid), 1624 (C=O, amide), 1450 (C—C, aromatic), 1305 (C—O, acid), 1305 (C—N), 750 (C—H, aromatic).

$^1$H NMR (300 MHz, CDCl$_3$) δ$_H$ (ppm) 0.94 (t, J=6.3 Hz, 3H, CH$_{3\ pentyl}$), 1.38-1.43 (m, 4H, 2×CH$_2$), 1.80-1.95 (m, 2H, CH$_2$), 4.18 (t, J=7.1 Hz, 2H, NCH$_2$), 6.97 (t, J=6.8 Hz, 1H), 7.11 (d, J=8.3 Hz, 1H), 7.45-7.67 (m, 2H), 8.24 (s, 1H, NCH$_{py}$), 8.85 (s, 1H, CH$_{py}$), 11.35 (s, 1H, OH), 13.74 (bs, 1H, NH), proton from carboxylic acid group was not observed.

$^{13}$C NMR (75 MHz, CDCl$_3$) δ$_C$ (ppm) 13.8 (CH$_{3\ pentyl}$), 22.1 (CH$_2$), 28.9 (CH$_2$), 28.9 (CH$_2$), 52.0 (NCH$_2$), 117.0 (C$_q$), 118.1 (C$_q$), 119.1 (CH$_{aro}$), 119.2 (C$_q$), 119.6 (CH$_{aro}$), 131.6 (CH$_{aro}$), 137.2 (CH$_{aro}$), 145.0 (CH$_{py}$), 146.0 (NCH$_{py}$), 162.8 (C$_q$), 163.9 (C$_q$, amide), 164.2 (C$_q$, acid), 194.1 (C$_q$, ketone).

HRMS (ESI$^+$) calcd for C$_{18}$H$_{20}$NO$_5$ [M+H]$^+$ 330.1341, found 330.1449.

The effect of CPADAML16 was tested on Wnt and TGF beta signaling and as shown in FIGS. 1A-1C, this compound remarkably inhibited both pathways. By comparison, none of Wnt or TGF beta inhibitors had affected the Hippo pathway reporter. Based on this, CPADAML16 may represent a unique candidate molecule to target simultaneously the Hippo, Wnt and TGF beta pathways.

Putative Mechanism(s) by which CPADAML16 Function

Figure 2A:
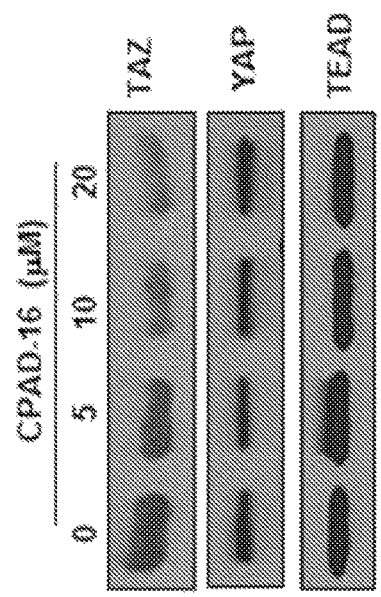
Figure 2D:
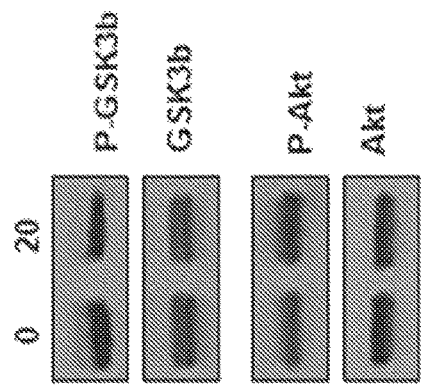
Figure 2C:
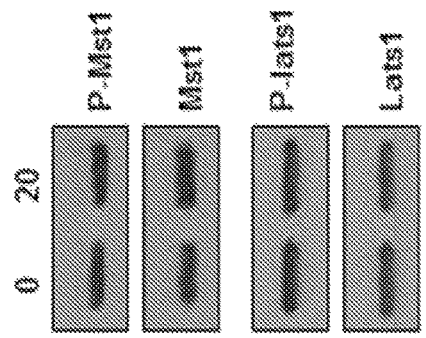

The ability of CPADAML16 to regulate the three transducers of the Hippo pathway namely, YAP, TAZ and TEAD was determined and as shown in FIG. 2A, Taz levels were reduced in a concentration dependent manner while those of YAP and TEAD were largely unaltered. Further results indicated that the decreased levels of TAZ could be due to its degradation and not inhibition of its expression. There are three possibilities by which this might occur (FIG. 2B): 1) through activation Mst/Lats, 2) inhibition of Akt or 3) activation of AMPK. We first analyzed the effect of CPADAML16 on activation of the Hippo core kinases MST1 and Lats1 and as shown in FIG. 2C, this compound did not affected phosphorylation of these enzymes. In light of recent findings that TAZ is also target of the GSK3 beta associated destruction complex, we reasoned that CPADAML16 may act directly or indirectly to activate this complex. The results show (FIG. 2D) that this compound inhibited phosphorylation (induced activation) of GSK3. This effect was not due to reduced phosphorylation of Akt, a known upstream inhibitor of GSK3 beta (FIG. 2D), suggesting that other elements of the AMPK/mTOR pathway could be implicated. Indeed, we found that CPADAML16 strongly induced phosphorylation of the tumor suppressor and energy sensor AMPK at threonine 172 (FIGS. 3A and 3B). These effects were concentration and time dependent and valid in various cell lines (FIG. 3C). Interestingly, CPADAML16 was more potent than AICAR, a well-known activator of AMPK (FIG. 3B). Together these findings identified AMPK as a novel target of CPADAML16, shedding light on a new mechanism by which this compound could signal for TAZ degradation and inhibition of Hippo signaling.

Effect of CPADAML16 on EMT, Cancer Cell Migration, Proliferation and Resistance to Therapy We found that CPADAML16 strongly inhibits cell migration (FIG. 4A) and the proliferation of three melanoma and one breast cancer cell lines (FIG. 4B). Since the development of resistance has been shown to be associated with EMT, we sought to determine whether CPADAML16 affects this process as well. The data presented in Figure (FIG. 4C) shows that melanoma cell response to doxorubicin was significantly enhanced in the presence of this compound suggesting that it may also suppresses drug resistance.

In Vivo Anti-Tumor Activity

Figure 5A:
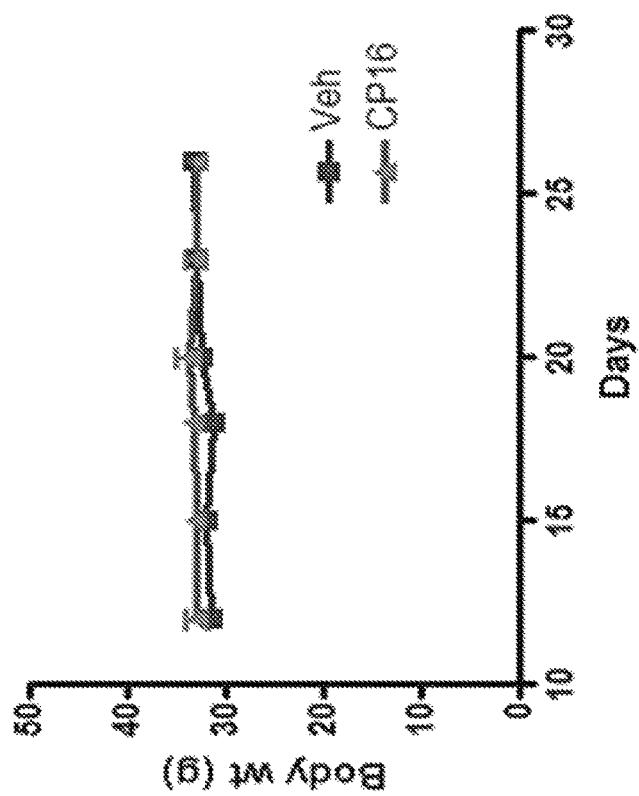
FIGS. 5A-5B. Effect of CPADAML16 (20 mg/kg) on tumor growth (FIG. 5A) and body weight (FIG. 5B). Data represents 7 replicates ±SE.
Figure 5B:
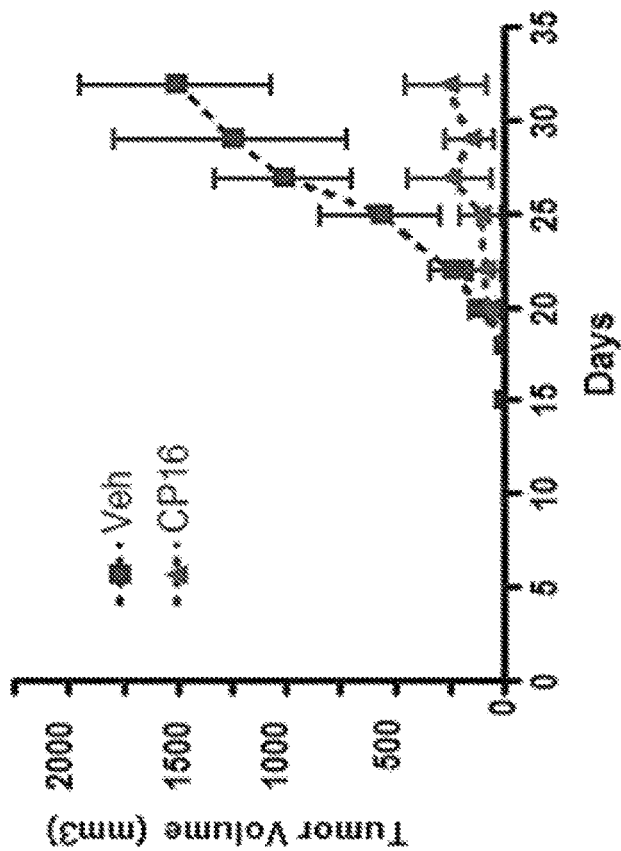

Experiments were carried out to analyse the anti-tumor activity and safety of CPADAML16 in mice bearing xenograft tumors. For this, nude mice (strain CD1) were subcutaneously inoculated with melanoma cells WM266 and after tumors became palpable, they were randomized into control and treatment groups and received 3 injections (starting on day 15 and separated by three days) of vehicle (control group) or CPADAML16 dissolved in the vehicle solution (treatment groups). Tumor volumes and body weight were measured and mice evaluated for signs of toxicity on a daily basis. At the end of experiments, the animals were sacrificed and tumors harvested to determine if molecular targets of CPADAML16 were altered. The results (FIG. 5A) show that CPADAML16 at 20 mg/Kg inhibited tumor growth by about 90% at the end of experiment. Mice in both control and treatment groups were in good health throughout the experiment and their body weight did not change significantly (FIG. 5B). The results suggest that CPADAML16 may represent a promising agent to treat cancer and warrant further preclinical and clinical investigation to establish its efficacy.

Overall, we have shown that CPADAML16 inhibits all three EMT pathways (Wnt, TGF beta and Hippo) and by doing so, it inhibited cancer cell migration, proliferation and resistance to therapy.

In view of the many possible embodiments to which the principles of the disclosed invention may be applied, it should be recognized that the illustrated embodiments are only preferred examples of the invention and should not be taken as limiting the scope of the invention.

What is claimed is:

1. A compound, or a pharmaceutically acceptable salt or stereoisomer thereof, of Formula I:

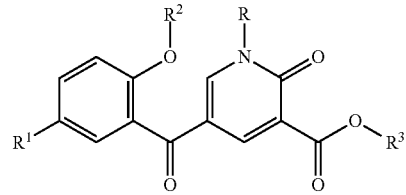

Formula I wherein R is —$(CH_2)_a$—Ar, wherein a is 1 to 6 and Ar is an aryl, substituted aryl, heteroaryl or substituted heteroaryl;
$R^1$ is hydrogen, alkoxy, or substituted alkoxy;
$R^2$ is alkyl or substituted alkyl; and
$R^3$ is hydrogen, alkyl, or substituted alkyl.

2. The compound of claim 1, wherein Ar is phenyl or substituted phenyl.
3. The compound of claim 1, wherein R is benzyl or substituted benzyl.
4. The compound of claim 1, wherein R is benzyl.
5. The compound of claim 1, wherein $R^1$ is hydrogen.
6. The compound of claim 1, wherein $R^2$ is $C_1$-$C_6$ alkyl.
7. The compound of claim 1, wherein $R^3$ is $C_1$-$C_6$ alkyl.
8. The compound of claim 1, wherein $R^3$ is ethyl.
9. A pharmaceutical composition comprising a compound of claim 1, and a pharmaceutically acceptable excipient.
10. The compound of claim 1, wherein the compound is:

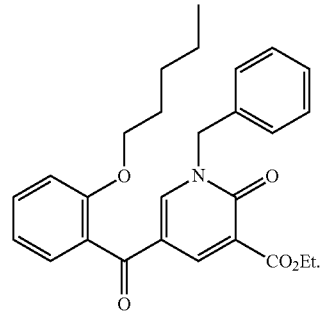 [SMILES: CCCCCOc1ccccc1C(=O)c1cc(C(=O)OCC)c(=O)n(Cc2ccccc2)c1]

11. The compound of claim 4, wherein $R^2$ is $C_1$-$C_6$ alkyl.
12. The compound of claim 11, wherein $R^3$ is ethyl.
13. The compound of claim 8, wherein $R^2$ is $C_1$-$C_6$ alkyl.
14. The compound of claim 13, wherein $R^3$ is ethyl.
15. The compound of claim 1, wherein $R^2$ is alkyl.
16. The compound of claim 1, wherein $R^3$ is alkyl or substituted alkyl.
17. The compound of claim 16, wherein $R^2$ is alkyl or substituted alkyl.
18. The compound of claim 1, wherein $R^2$ is pentyl.
19. The compound of claim 2, wherein $R^2$ is pentyl.

* * * * *